(12) United States Patent
Buck et al.

(10) Patent No.: US 9,388,250 B2
(45) Date of Patent: Jul. 12, 2016

(54) METHOD TO TREAT PSORIASIS AND OTHER HYPERPROLIFERATIVE SKIN DISORDERS

(75) Inventors: Jochen Buck, Old Greenwich, CT (US); Lonny Levin, New York, NY (US); Jonathan Zippin, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/202,919

(22) PCT Filed: Feb. 23, 2010

(86) PCT No.: PCT/US2010/025102
§ 371 (c)(1),
(2), (4) Date: Aug. 23, 2011

(87) PCT Pub. No.: WO2010/096830
PCT Pub. Date: Aug. 26, 2010

(65) Prior Publication Data
US 2011/0305640 A1  Dec. 15, 2011

Related U.S. Application Data

(60) Provisional application No. 61/154,653, filed on Feb. 23, 2009.

(51) Int. Cl.
| | | |
|---|---|---|
| *A61K 31/427* | (2006.01) | |
| *A61K 31/4184* | (2006.01) | |
| *A61K 31/4152* | (2006.01) | |
| *A61K 31/4015* | (2006.01) | |
| *A61K 31/496* | (2006.01) | |
| *A61K 31/421* | (2006.01) | |
| *C07K 16/40* | (2006.01) | |

(52) U.S. Cl.
CPC ............... *C07K 16/40* (2013.01); *A61K 31/427* (2013.01)

(58) Field of Classification Search
None
See application file for complete search history.

(56) References Cited

U.S. PATENT DOCUMENTS

| 7,449,459 B2 * | 11/2008 | Buchmann et al. ........ 514/232.8 |
| 2005/0287570 A1 | 12/2005 | Mounts |
| 2006/0074084 A1 | 4/2006 | Nguyen et al. |
| 2007/0244174 A1 | 10/2007 | Buck et al. |

FOREIGN PATENT DOCUMENTS

| WO | 2006/113236 A1 | 10/2006 |
| WO | 2007/010285 A2 | 1/2007 |
| WO | WO 2008088771 A2 * | 7/2008 |
| WO | 2008/121171 A1 | 10/2008 |

OTHER PUBLICATIONS

Schmid et al. Journal of General Physiology, 130(1) Jul. 2007, p. 99-109.*
Delescluse et al. Differentiation vol. 2, p. 343-350, 1974.*
Kapas et al. Eur J Biochem 256, p. 75-79, 1998.*
Funding, A.T. et al., "Mitogen- and Stress-Activated Protein Kinase 2 and Cyclic AMP Response Element Binding Protein are Activated in Lesional Psoriatic Epidermis", J Investigative Dermatology (2007), vol. 127:8, pp. 2012-2019.
Zippin, J. H. et al., "Bicarbonate-responsive "soluble" adenylyl cyclase defines a nuclear cAMP microdomain", J. Cell Biology (2004), vol. 164:4, pp. 527-534.
Hallows, K.R. et al., "Regulation of Epithelial Na+ Transport by Soluble Adenylyl Cyclase in Kidney Collecting Duct Cells", J. Bio. Chem. (2009), vol. 284:9, pp. 5774-5783.
Müller, A. et al., "Cooperative Activation of Human Papillomavirus Type 8 Gene Expression by the E2 Protein and the Cellular Coactivator p300", J. of Virology, (2002), vol. 76:21, pp. 11042-11053.

* cited by examiner

*Primary Examiner* — Nissa Westerberg
(74) *Attorney, Agent, or Firm* — Kenyon & Kenyon LLP

(57) ABSTRACT

Soluble adenylyl cyclase (sAC) is implicated in proliferation of keratinocytes. Inhibitors of sAC are useful for the treatment and/or prevention of psoriasis and other hyperproliferative skin disorders. Assays to identify such compounds are also described.

5 Claims, 14 Drawing Sheets

METHOD TO TREAT PSORIASIS AND OTHER HYPERPROLIFERATIVE SKIN DISORDERS

CROSS REFERENCE TO RELATED APPLICATIONS

The present invention claims the benefit of the following U.S. Provisional Patent Application No. 61/154,653 filed Feb. 23, 2009. The contents of this application are incorporated herein by reference.

GOVERNMENT FUNDING AND RIGHTS

This invention was made with United States Government support under NIH Grant GM62328. The United States Government has certain rights in the invention.

FIELD OF THE INVENTION

The present invention is directed to the treatment of psoriasis and other hyperproliferative skin disorders. This treatment may use inhibitors of soluble adenylyl cyclase (sAC).

BACKGROUND

The pathogenesis of psoriasis has been extensively discussed for decades. Initial research focused on a keratinocyte role in the disease; in fact, until the early 1980s, psoriasis was treated as a disease primarily of keratinocytes[1,2]. Early work also suggested that second messenger signaling pathways, namely cAMP, was important, but a clear source or role for cAMP was never firmly established[1]. Subsequently, it became apparent that the immune system, namely T-cells, play an essential role in the development of psoriasis[2]. These data have led to the development of numerous biological and chemical therapeutics, which have greatly improved the treatment of severe psoriasis and non-skin manifestations of psoriasis such as arthritis.

Specifically there are three modalities to treat psoriasis; topical, systemic (including antimetabolites and biologics), and phototherapy. sAC inhibitors, which can block psoriatic pathophysiology, represent a new class of psoriasis therapeutics.

Topical and systemic psoriatic therapeutics function by either blocking the immune system which is responsible for secreting activating factors that stimulate keratinocyte growth or by directly inhibiting keratinocyte turnover.

Topical therapies include corticosteroids, keratolytics, anthralin, coal tar, Vitamin D analogs, and retinoids.

For steroids (corticosteroids), typically a high potency steroid is required and is applied daily. While the exact mechanism of action of topical steroids in psoriasis is largely unknown, steroids are thought to be anti-inflammatory, immunosuppressive, and antiproliferative.

Keratolytics, such as salicylic acid, work by removing scale from the psoriatic lesion. This class of medication does not affect the underlying cause of the psoriasis so the disease will remain, but the psoriasis will be less scaly. By reducing scale, other medications are able to penetrate the plaques of psoriasis more easily allowing for greater efficacy.

Anthralin and Coal tar both appear to have anti-proliferative and anti-inflammatory properties although the exact mechanism of either is not known. They both suffer from being very messy and smelly. Anthralin turns skin and fabric purple while tar stains everything black. For these reasons, patient compliance is very low.

Vitamin D analogs were first employed when physicians noticed that patients with psoriasis and altered serum calcium levels had a resolution of their psoriasis when calcium levels were normalized. Later data found that the bioactive form of Vitamin D,1,25-dihydroxycholecalciferol, has been shown to inhibit keratinocyte proliferation and promote differentiation. This topical medication is commonly used in conjunction with topical steroids. Theoretical risks of overuse include hypercalcemia.

Retinoids mediate cell differentiation and proliferation. Retinoids, specifically tazarotene, is applied topically on a daily basis and has been demonstrated to have efficacy in psoriasis. Retinoids are contraindicated in pregnancy and can be very irritating to the skin.

Therefore, dermatologists and patients would benefit from new topical therapies for psoriasis.

Epidermal hyperplasia can occur secondary to a number of stimuli. These stimuli can be separated into congenital genetic alterations, infectious, inflammatory, and cell-cycle/apoptotic dysregulation as seen within the spectrum of epidermolytic hyperkeratosis, human papilloma virus (HPV), psoriasis, and skin cancer, respectively. Although each of these skin diseases is induced by a varied set of stimuli, they all are defined by the proliferation of keratinocytes. Keratinocyte proliferation requires alteration in programmed differentiation along with induction of the cell cycle. Cellular differentiation and cell cycle are modulated by numerous signaling pathways, and hyperstimulation or dysregulation of these pathways represents key events leading to many diseases of epidermal hyperplasia. The cyclic adenosine monophosphate (cAMP)-signaling pathway is integral to both cellular differentiation and proliferation, and has been implicated in the pathogenesis of diseases of epidermal hyperplasia such as psoriasis[1,3,4,5,6].

The signaling molecule cAMP has long been studied in the epidermis. cAMP and its effector proteins, such as protein kinase-A (PKA) and cAMP-response-element-binding protein (CREB), have known roles in the cells of the epidermis and dermis, including keratinocytes, melanocytes, eccrine ductal cells, and fibroblasts[7]. In many cases the initiating stimulus for these cAMP-dependent pathways are well established; for example, the melanocyte-stimulating hormone-induced cAMP pathways in melanocytes[8]. In other cases, the stimuli leading to cAMP signal transduction are less clear.

In the present invention the role of keratinocytes and the connection to cAMP signaling with respect to psoriasis is described. There is a newly discovered source of cAMP, called bicarbonate-responsive adenylyl cylcase (brAC) and also called soluble adenylyl cyclase (sAC). sAC is unlike the more widely studied G-protein activated, transmembrane adenylyl cyclases (tmACs). sAC is insensitive to G-proteins and instead is regulated by bicarbonate ions, calcium ions, and ATP[9]. Because of its regulation by ATP and bicarbonate, a byproduct of $CO_2$, this enzyme functions as a metabolic sensor[10,11]. In addition, unlike tmACs, which are permanently linked to the plasma membrane, sAC is present in the nucleus, where it regulates gene expression[12]; the mitochondria, where it influences oxidative phosphorylation[13]; and on the cytoskeleton, particularly the centrioles, where it is predicted to affect the cell cycle[12,14]. The genetic location of human sAC at 1q24[15], a psoriasis genetic locus, and its stimulation by TNF[16], an integral effector in psoriasis pathogenesis.

Because cAMP has an integral role in the proliferation, differentiation, and expression of key proteins in keratinocytes, the expression and localization of sAC protein in normal human skin and diseased skin provides new methods for treating skin disorders. In the present invention it is described that sAC is upregulated in the nuclei of keratinocytes in certain hyperproliferative skin diseases, including psoriasis and squamous cell carcinoma (SCC) in situ, whereas sAC is lost from the nucleus when a malignant epithelial tumor acquires invasive properties in the dermis. Accordingly, this application provides methods of treatment of skin disorders by administering inhibitors of sAC.

The inventors and others have previously described inhibitors of sAC as well as methods to identify modulators of sAC (for small molecules see published PCT applications WO2005070419, WO2008121171, WO2008088771, and WO2006113236 and US published application US2006074084; for monoclonal antibodies see references Chen et al.[9], Zippin et al.[14], and Buck et al.[17]; for RNAi see published PCT application WO2005070419). Each reference is incorporated herein by reference in its entirety).

SUMMARY OF THE INVENTION

In one aspect, the present invention features a method to inhibit keratinocyte replication by administering a composition that inhibits soluble adenylyl cyclase in a keratinocyte.

The composition may comprise an antibody, a nucleic acid, or a small molecule selected from the group consisting of Gossypol, 4-hydroxyestradiol, 2-hydroxyestradiol, 2-hydroxyestrone, 2-benzimidazolylthioacetamide-N-ethyl-2-benzyl (KH7.102), the compound of formula I (KH1)

formula I

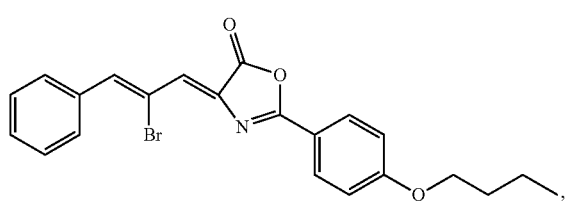

the compound of formula II (KH2)

formula II

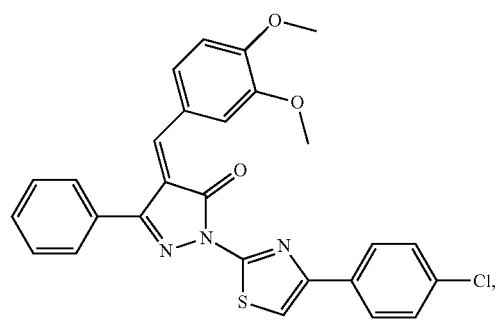

the compound of formula III (KH3)

formula III

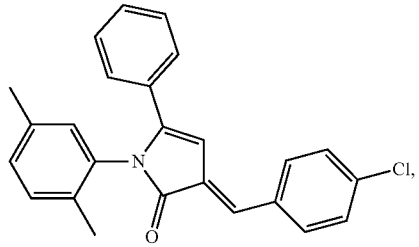

the compound of formula IV (KH4)

formula IV

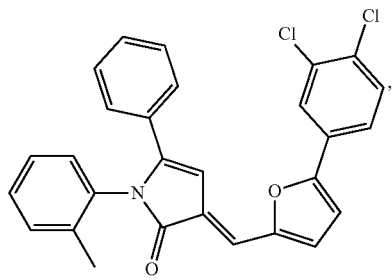

the compound of formula V (KH8)

formula V

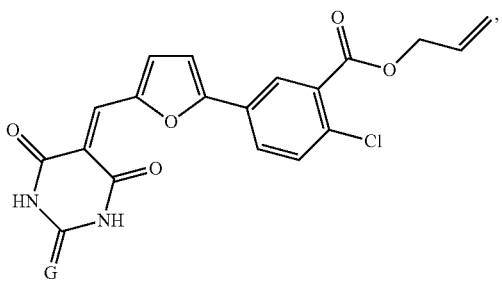

the compound of formula VI (KH7.120)

formula VI

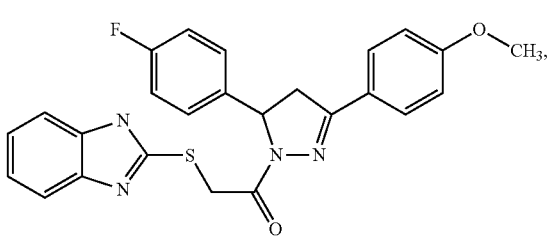

and a compound of formula VII

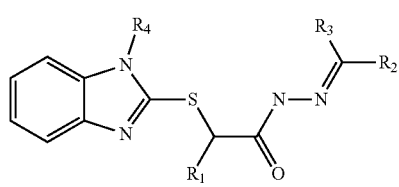

formula VII wherein $R_1$ and $R_3$ are each independently H or a $C_{1-4}$ alkyl $R_2$ is a $C_{6-8}$ aryl, naphthalene or a $C_{4-5}$ heteroaryl having at least one hetero atom selected from N, S and O, the phenyl or $C_{4-5}$ heteroaryl optionally substituted with one or more radicals selected from the group consisting of hydroxyl, halogen, nitro, $C_{1-4}$ alkyl, $C_{1-4}$ alkoxy, $C_{1-4}$ carboxyl, phenyl, $C_{1-4}$ alkoxy phenyl, and a halogenated $C_{1-4}$ alkyl such as for example trifluoromethyl, and $R_4$ is H, a $C_{1-4}$ alkyl, a $C_{1-4}$ carboxyl or a $C_{6-8}$ aryl, optionally substituted with a $C_{1-4}$ alkyl, a $C_{1-4}$ alkoxy, hydroxyl or a halogen. The $C_{6-8}$ aryl may be phenyl and the $C_{4-5}$ heteroaryl may be a pyridine, furan, or thiophene.

The small molecule may be selected from table 2 provided herein. The nucleic acid may be RNA, and may be one of two sequences described herein. The inhibitor may be administered topically, injected intradermally or epidermally, or administered systemically. Systemic administration may be enteral or parenteral administration, including oral administration.

In another aspect, the present invention features a method to treat a skin disorder with symptoms comprising thickening of the epidermis, by administering a composition that inhibits soluble adenylyl cyclase. The disorder may be selected from the group comprising: Psoriasis; Psoriasis vulgaris (including Nummular psoriasis and Plaque psoriasis); Generalized pustular psoriasis (including Impetigo herpetiformis and Von Zumbusch's disease); Acrodermatitis continua; Pustulosis palmaris et plantaris; Guttate psoriasis; Arthropathic psoriasis; Other psoriasis (including inverse psoriasis); actinic keratoses; squamous cell carcinoma in situ; and squamous cell carcinoma. The disorder may be induced by human papillomavirus, and if so may be selected from the group comprising: verruca vulgaris, condyloma accuminata, flat warts, butcher's warts, and epidermodysplasia verruciformis. The composition may comprise an antibody, a nucleic acid, or a small molecule selected from the group consisting of Gossypol, 4-hydroxyestradiol, 2-hydroxyestradiol, 2-hydroxyestrone, 2-benzimidazolylthioacetamide-N-ethyl-2-benzyl (KH7.102), the compound of formula I (KH1)

formula I the compound of formula II (KH2)

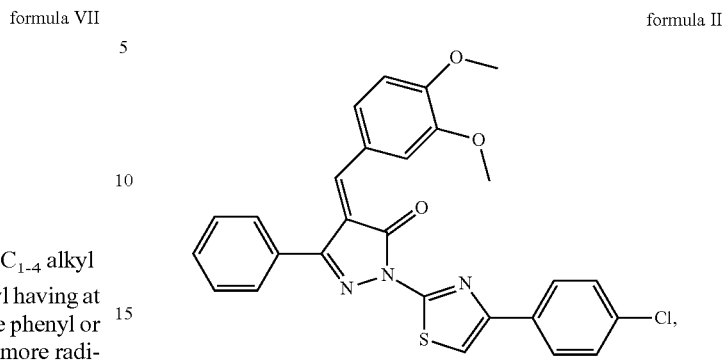

formula II the compound of formula III (KH3)

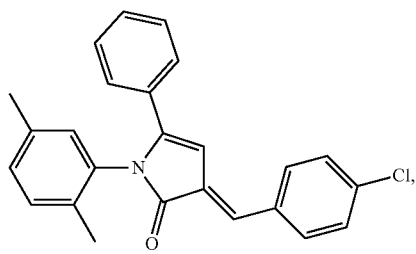

formula III the compound of formula IV (KH4)

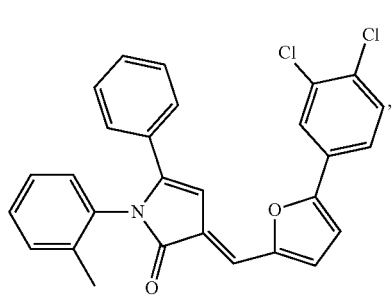

formula IV the compound of formula V (KH8)

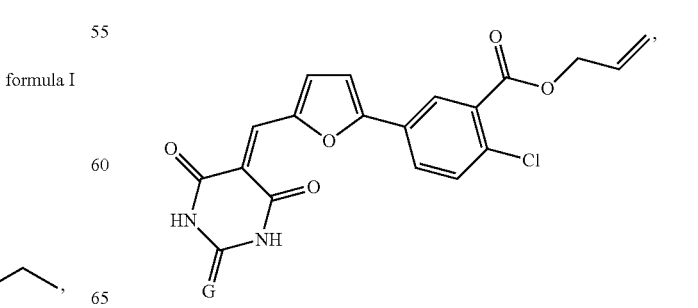

formula V the compound of formula VI (KH7.120)

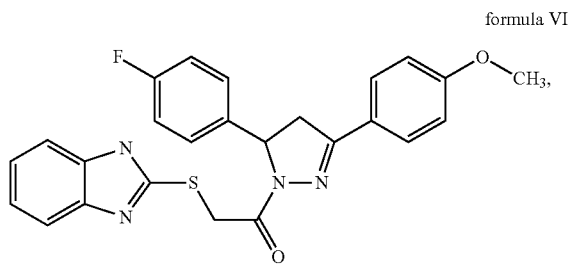 [SMILES: COc1ccc(C2=NN(C(=O)CSc3nc4ccccc4[nH]3)C(c3ccc(F)cc3)C2)cc1]

formula VI and a compound of formula VII

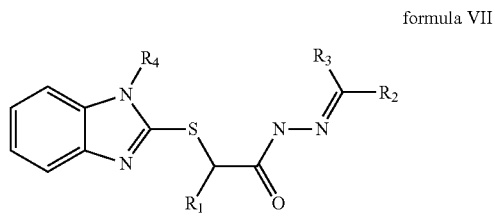

formula VII wherein $R_1$ and $R_3$ are each independently H or a $C_{1-4}$ alkyl $R_2$ is a $C_{6-8}$ aryl, naphthalene or a $C_{4-5}$ heteroaryl having at least one hetero atom selected from N, S and O, the phenyl or $C_{4-5}$ heteroaryl optionally substituted with one or more radicals selected from the group consisting of hydroxyl, halogen, nitro, $C_{1-4}$ alkyl, $C_{1-4}$ alkoxy, $C_{1-4}$ carboxyl, phenyl, $C_{1-4}$ alkoxy phenyl, and a halogenated $C_{1-4}$ alkyl such as for example trifluoromethyl, and $R_4$ is H, a $C_{1-4}$ alkyl, a $C_{1-4}$ carboxyl or a $C_{6-8}$ aryl, optionally substituted with a $C_{1-4}$ alkyl, a $C_{1-4}$ alkoxy, hydroxyl or a halogen. The $C_{6-8}$ aryl may be phenyl and the $C_{4-5}$ heteroaryl may be a pyridine, furan, or thiophene. The small molecule may be selected from table 2 provided herein. The nucleic acid may be RNA, and may be one of two described sequences. The inhibitor may be administered topically, injected intradermally or epidermally, or administered systemically. Systemic administration may be enteral or parenteral administration, including oral administration.

In another aspect, the present invention features an assay for identifying drug candidates to treat a skin disorder with symptoms including thickening of the epidermis, abnormal replication of the cells contained within the epidermis, and recruitment of immunocytes in response to replication of the cells contained within the epidermis or thickening of the epidermis. The assay comprises testing a compound's ability to antagonize/inhibit soluble adenylyl cyclase activity, wherein compounds that inhibit soluble adenylyl cyclase activity are such drug candidates. In said assay, the soluble adenylyl cyclase activity may be measured by measuring the amount of cAMP that is present. The assay may be cell-free, conducted using cells cultured in vitro, or conducted on a live animal. cAMP levels may be raised by administering IL-22.

DETAILED DESCRIPTION OF THE INVENTION

Although sAC exists as a cytosolic protein, sAC can translocate into the nucleus, where it regulates cAMP-mediated gene expression. Using an in vitro MDCK epithelial differentiation model, the present invention provides that sAC protein, along with key cAMP-dependent proteins essential for gene expression, transitioned from diffusely cytosolic and nuclear to almost exclusively nuclear in proliferating cells. Nuclear translocation occurs when cells become hyperproliferative either by genetic changes or incubation with an activator. sAC is an essential protein for the growth of hyperstimulated cells, inhibitors of sAC arrest the cell cycle of hyperstimulated cells. This effect is not permanent as washing out of sAC inhibitory small molecules allows cells to reenter the cell cycle.

In disease states characterized by symptoms comprising hyperproliferative keratinocytes and associated immunocyte infiltration, such as without limitation squamous cell carcinoma in skin, verruca vulgaris, and psoriasis, sAC is enriched in the nucleus. Therefore, inhibition of sAC is useful for treating a wide range of skin diseases.

Figure 12:
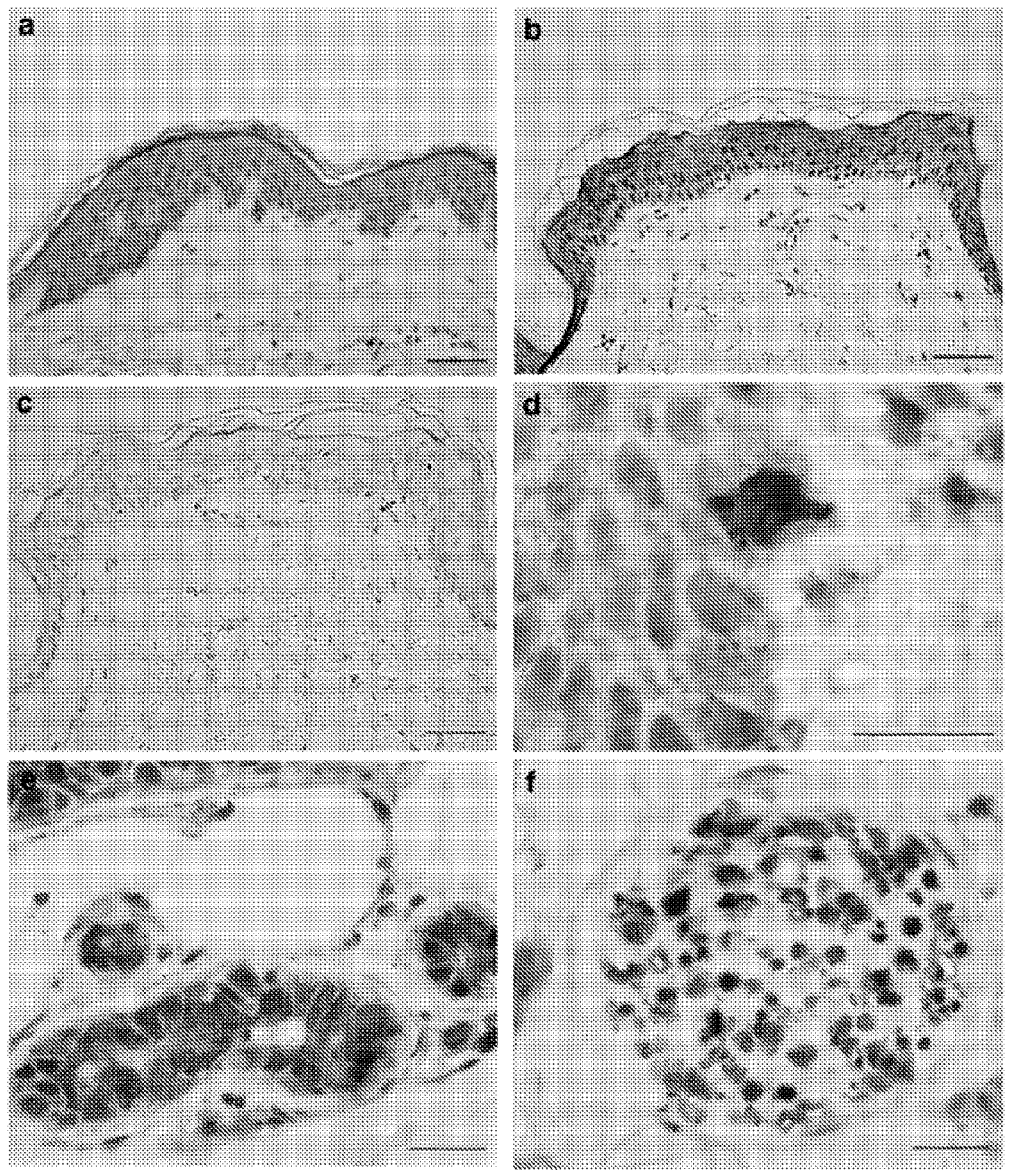
FIG. 12 Immunostaining of sAC in normal skin. (a) Hematoxylin (blue) and eosin (red) staining of normal human skin. (b) Normal human skin immunostained with R21 (red) and hematoxylin (blue). (c) Normal human skin immunostained with R21+ blocking peptide (red) and hematoxylin (blue). (d) Normal epidermis immunostained with R21 (red), Melan-A (brown), and hematoxylin (blue). (e) Normal human skin eccrine duct immunostained with R21 (red) and hematoxylin (blue). (f) Normal human skin cutaneous nerve immunostained with R21 (red), PGP9.5 (brown), and hematoxylin (blue). Bars=50 µm (a-c) and 10 µm (d-f).
Figure 16:
FIG. 16 Nuclear sAC is enhanced in psoriatic skin and is associated with phosphorylated CREB. (a) Hematoxylin (red) and eosin (blue) staining of psoriatic lesional skin. (b) Psoriatic lesional skin immunostained with R21 (red) and hematoxylin (blue). The inset is a magnified view of a portion of the epidermis demonstrating that some nuclei are positive for sAC (white arrow) and some are negative for sAC (black arrow). (c) Psoriatic lesional skin immunostained with R21 (red) and an antibody against phosphorylated CREB (light blue). Panel c and inset: Nuclei positive for both sAC and phosphorylated CREB appear dark blue to purple (gray arrows). White arrows indicate nuclei positive for phosphorylated CREB only (light blue). Black arrows indicate nuclei positive for sAC only (red). Bars=50 µm.

In the present invention localization of sAC in normal human skin reveals the protein to be diffusely expressed in keratinocytes and melanocytes of the epidermis, eccrine ductal cells, mononuclear cells, and cutaneous nerves. In particular sAC is localized nuclear during cellular proliferation and is absent from the nucleus when cells differentiate. As the skin loses dead cells from the cornified layer, new cells are replaced from below. In normal skin, cell division occurs both at the basal cell layer and immediately above the basal cell layer, which consists of a group of cells called transient amplifying cells. Consistent herewith is that sAC nuclear staining in normal skin to occur primarily in the lower levels of the epidermis (FIG. 12). While basal cell layer stem cells can divide forever, their rate of division is very slow compared with that of transient amplifying cells, which have a finite proliferative potential. In psoriasis, the transient amplifying cell layer is thought to represent the group of keratinocytes, which respond to inflammatory cytokines and lead to skin lesions. In the present invention the strongest sAC nuclear staining in psoriasis lesions is in a band of keratinocytes above the basal cell layer and below the upper layers of the epidermis where cells are beginning to differentiate (FIG. 16b).

Therefore, the present invention provides that inhibition of sAC is useful for treating a wide range of skin diseases. Further, IL-22 has a known association with psoriasis[18]. IL-22 can be used to induce acanthosis and other psoriasis pathogenic events in vivo. The present invention provides that blocking of sAC interferes with the signal transduction pathway initiated by IL-22 in keratinocytes.

Further, IL-22 functions not only to induce acanthosis but also to recruit other immunocytes and perpetuate an inflammatory response. In other skin diseases an inflammatory response mediated by T cells does not necessarily lead to acanthosis. One such example is atopic dermatitis where TH17 cells have been found and are known to induce key alterations in keratinocytes. Therefore, the ability to block the effects of IL-22 in keratinocytes has efficacy in TH17 dependent dermatiditis.

In addition to the evidence linking TH17 cells and IL-22 effects to psoriasis pathogenesis, this inflammatory cascade has been detected in other tissue besides skin and in epithelial cells other than keratinocytes. Therefore inhibitors of sAC are useful to treat a range of conditions initiated by pathological IL-22 signalling in epithelial cells, including inflammatory bowel diseases (IBD) such as ulcerative colitis (UC) and Crohn's disease (CD) as well as other inflammations of the GI system such as gastroenteritis, ileitis, colitis, appendicitis, coeliac disease, and irritable bowel syndrome; inflammatory lung conditions[19], and others.

The subject suffering the disease for which the present invention provides a method of treatment can be any animal, such as a bird, a fish, a reptile, or a mammal. The subject may also be livestock such as, cattle, swine, sheep, poultry, and horses, or pets, such as dogs and cats. The subject may be human.

The present invention also provides a method for the prevention or treatment of a disease characterized by symptoms comprising hyperproliferative keratinocytes in a subject, by administering to the subject a composition comprising a therapeutically effective amount of an inhibitor of soluble adenylyl cyclase and a pharmaceutically acceptable excipient.

The composition of the present invention for administering a therapeutically effective amount of an inhibitor of sAC may comprise an antibody, a nucleic acid, or a small molecule selected from the group consisting of Gossypol, 4-hydroxyestradiol, 2-hydroxyestradiol, 2-hydroxyestrone, 2-benzimidazolylthioacetamide-N-ethyl-2-benzyl (KH7.102), the compound of formula I (KH1)

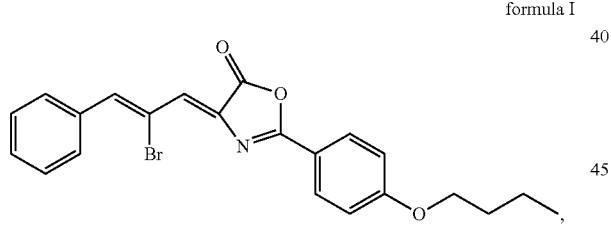

the compound of formula II (KH2)

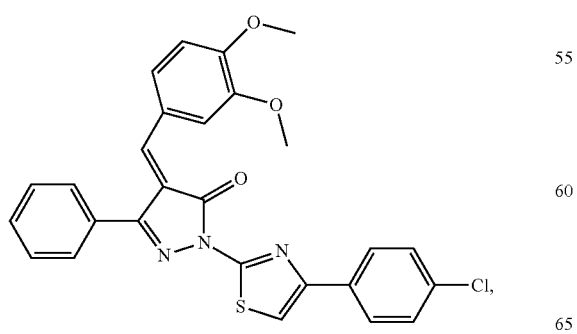

the compound of formula III (KH3)

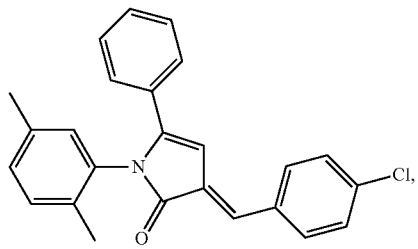

the compound of formula IV (KH4)

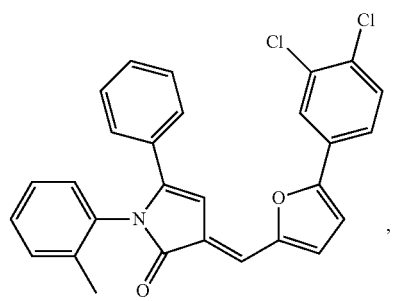

the compound of formula V (KH8)

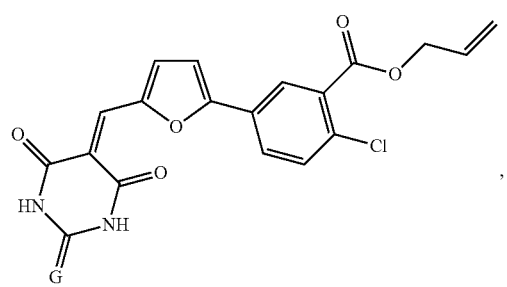

the compound of formula VI (KH7.120)

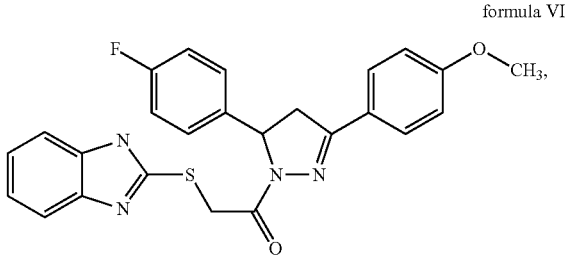 [SMILES: COc1ccc(C2=NN(C(=O)CSc3nc4ccccc4[nH]3)C(c3ccc(F)cc3)C2)cc1]

and a compound of formula VII

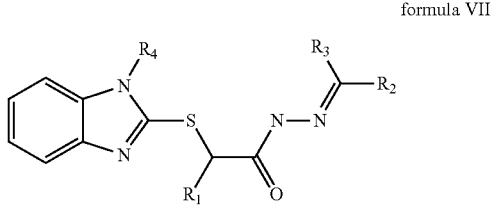

formula VII wherein $R_1$ and $R_3$ are each independently H or a $C_{1-4}$ alkyl $R_2$ is a $C_{6-8}$ aryl, naphthalene or a $C_{4-5}$heteroaryl having at least one hetero atom selected from N, S and O, the phenyl or $C_{4-5}$heteroaryl optionally substituted with one or more radicals selected from the group consisting of hydroxyl, halogen, nitro, $C_{1-4}$ alkyl, $C_{1-4}$ alkoxy, $C_{1-4}$ carboxyl, phenyl, $C_{1-4}$ alkoxy phenyl, and a halogenated $C_{1-4}$ alkyl such as for example trifluoromethyl, and $R_4$ is H, a $C_{1-4}$ alkyl, a $C_{1-4}$ carboxyl or a $C_{6-8}$ aryl, optionally substituted with a $C_{1-4}$ alkyl, a $C_{1-4}$ alkoxy, hydroxyl or a halogen. The $C_{6-8}$ aryl may be phenyl and the $C_{4-5}$ heteroaryl may be a pyridine, furan, or thiophene.

The small molecule may be selected from table 2 provided herein. Those in the art will appreciate that the small molecule/compound for use in the method of the invention including those described by any of the formulas may also be in the form of a pharmaceutically acceptable salt, ester, amide, solvate or prodrug thereof. The nucleic acid may be RNA, and may be one of two sequences described herein.

In another aspect, the present invention provides pharmaceutically acceptable compositions which comprise a therapeutically-effective amount of one or more of the inhibitors of soluble adenylyl cyclase, as described above, formulated together with one or more pharmaceutically acceptable excipients. In another aspect, the present invention provides pharmaceutically acceptable compositions which comprise a therapeutically-effective amount of one or more of the inhibitors of soluble adenylyl cyclase, as described above, formulated together with one or more pharmaceutically acceptable excipients and other therapeutically effective medications known in the art allowing for but not limited to combination therapies to improve overall efficacy of each individual therapeutic or to limit the concentration of either therapeutic to avoid side effects and maintain efficacy. The active ingredient and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

A therapeutically effective amount of the pharmaceutical composition of the present invention is sufficient to treat or prevent a disease characterized by symptoms comprising hyperproliferative keratinocytes. The therapeutically effective amount may prevent the keratinocytes from proliferating. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of bacterial adenylyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

The present invention therefore provides novel approaches for the treatment of psoriasis and other disorders marked by abnormal or unwanted epidermal proliferation such as SCC and verruca vulgaris. The present invention provides for the treatment or prevention of a skin disorder with symptoms comprising thickening of the epidermis, by administering a composition that inhibits soluble adenylyl cyclase. The disorder may be selected from the group comprising: Psoriasis; Psoriasis vulgaris (including Nummular psoriasis and Plaque psoriasis); Generalized pustular psoriasis (including Impetigo herpetiformis and Von Zumbusch's disease); Acrodermatitis continua; Pustulosis palmaris et plantaris; Guttate psoriasis; Arthropathic psoriasis; Other psoriasis (including inverse psoriasis); actinic keratoses; squamous cell carcinoma in situ; and squamous cell carcinoma. The disorder may be induced by human papillomavirus, and if so may be selected from the group comprising: verruca vulgaris, condyloma accuminata, flat warts, butcher's warts, and epidermodysplasia verruciformis.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms. Preferred dosing is one administration per day.

In another aspect, the present invention provides a method to inhibit keratinocyte replication by administering a composition that inhibits soluble adenylyl cyclase in a keratinocyte. The composition may comprise an antibody, a nucleic acid, or a small molecule selected from the group consisting of Gossypol, 4-hydroxyestradiol, 2-hydroxyestradiol, 2-hydroxyestrone, 2-benzimidazolylthioacetamide-N-ethyl-2-benzyl (KH7.102), the compound of formula I (KH1)

the compound of formula II (KH2)

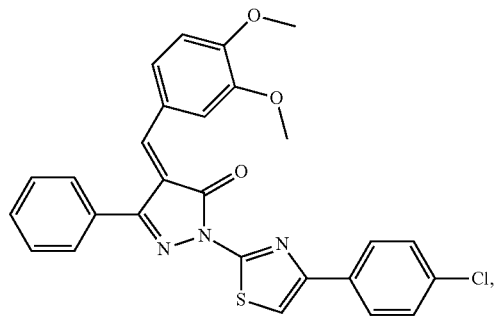

formula II the compound of formula III (KH3)

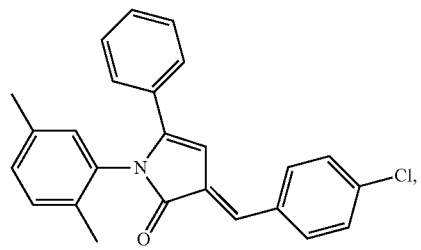

formula III the compound of formula IV (KH4)

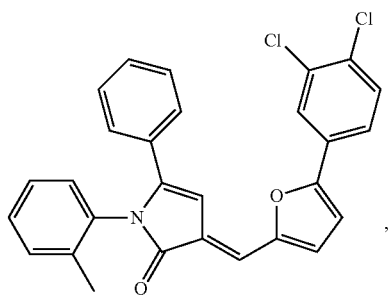

formula IV the compound of formula V (KH8)

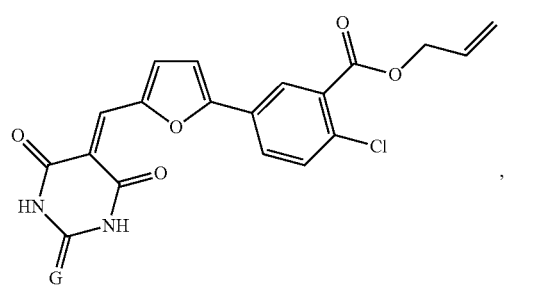

formula V

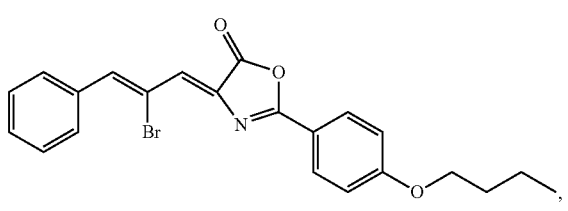

formula I the compound of formula VI (KH7.120)

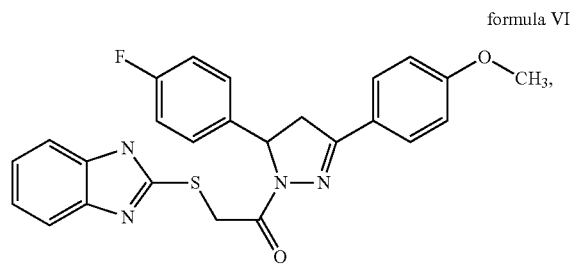 [SMILES: COc1ccc(C2=NN(C(=O)CSc3nc4ccccc4[nH]3)C(c3ccc(F)cc3)C2)cc1]

formula VI and a compound of formula VII

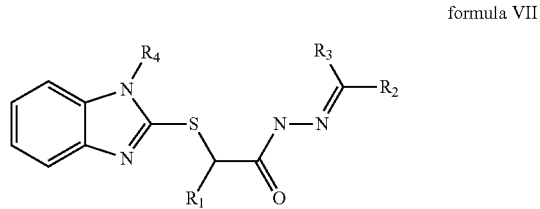

formula VII wherein $R_1$ and $R_3$ are each independently H or a $C_{1-4}$ alkyl $R_2$ is a $C_{6-8}$ aryl, naphthalene or a $C_{4-5}$ heteroaryl having at least one hetero atom selected from N, S and O, the phenyl or $C_{4-5}$ heteroaryl optionally substituted with one or more radicals selected from the group consisting of hydroxyl, halogen, nitro, $C_{1-4}$ alkyl, $C_{1-4}$ alkoxy, $C_{1-4}$ carboxyl, phenyl, $C_{1-4}$ alkoxy phenyl, and a halogenated $C_{1-4}$ alkyl such as for example trifluoromethyl, and $R_4$ is H, a $C_{1-4}$ alkyl, a $C_{1-4}$ carboxyl or a $C_{6-8}$ aryl, optionally substituted with a $C_{1-4}$ alkyl, a $C_{1-4}$ alkoxy, hydroxyl or a halogen. The $C_{6-8}$ aryl may be phenyl and the $C_{4-5}$ heteroaryl may be a pyridine, furan, or thiophene.

The small molecule may be selected from table 2 provided herein. Those in the art will appreciate that the small molecule/compound for use in the method of the invention including those described by any of the formulas may also be in the form of a pharmaceutically acceptable salt, ester, amide, solvate or prodrug thereof. The nucleic acid may be RNA, and may be one of two sequences described herein.

In another aspect, the present invention features an assay for identifying drug candidates to treat a skin disorder with symptoms including thickening of the epidermis, abnormal replication of the cells contained within the epidermis, and recruitment of immunocytes in response to replication of the cells contained within the epidermis or thickening of the epidermis. The assay comprises testing a compound's ability to antagonize soluble adenylyl cyclase activity, wherein compounds that inhibit soluble adenylyl cyclase activity are such drug candidates. In said assay, the soluble adenylyl cyclase activity may be measured by measuring the amount of cAMP that is present. The assay may be cell-free, conducted using cells cultured in vitro, or conducted on a live animal. cAMP levels may be raised by administering IL-22.

The assay of the present invention may comprise: a) providing a test cell, tissue or organism; b) raising cAMP levels in the test cell, tissue or organism by administering IL-22 to said test cell, tissue or organism; c) measuring the amount of cAMP present in the test cell, tissue or organism; d) administering the compound to the test cell, tissue or organism; e) measuring the amount of cAMP present in the test cell, tissue or organism; and f) determining the inhibitory effect of the compound on soluble adenylyl cyclase activity by observing a decrease of the amount of cAMP present in step e) compared to step c).

Having thus described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to limit its scope in any way.

EXAMPLES

Immunohistochemistry of Human Tissue

Cases were retrospectively identified using archival tissue from the database of the Division of Dermatopathology, Weill Medical College of Cornell University. The cases chosen included verruca vulgaris (9), MCV (7), seborrheic keratosis (10), epidermolytic hyperkeratosis (4), acanthosis nigricans (5), AKs (5), bowenoid papulosis (11), SCC both in situ and invasive (19), basal cell carcinoma (10), pityriais rubra pilaris (3), and psoriasis (17). For normal skin unremarkable sections of skin from excision specimens were chosen. Immunostaining of patient samples was approved under IRB protocol number 0710009479, Weill Cornell Medical Center, New York, N.Y. The study was conducted according to the Declaration of Helsinki Principles.

All steps were performed using the Leica Microsystems BondMax Autostainer (Bannockburn, Ill.). Formalin-fixed, paraffin-embedded samples were first baked at 60° C. for 30 minutes followed by a dewaxing procedure. Slides were treated with a Leica Microsystems Dewax solution (part number AR922) for 3 minutes at 72° C., then a Dewax solution wash at 72° C., and finally a Dewax solution wash at ambient temperature. This was followed by three washes with Ethyl Alcohol 200 proof (Pharmco-Aaper, Brookfield, Conn., cat. number 111000200) and three washes with Leica Microsystems Wash buffer (part number AR9590).

All sections were treated as follows for sAC immunostaining: following the dewaxing procedure, the samples were pretreated by two washes in Leica Microsystems HIER1 (part number AR9961), followed by HIER1 pretreatment for 30 minutes at 100° C., and then HIER1 pretreatment for 12 minutes at ambient temperature. Before immunostaining, the sections were blocked using the Dako Dual Endogneous Enzyme Block (part number 52003) for 5 minutes followed by three washes with Bond Wash Solution. The wash buffer (Bond Wash Solution) is used in all washing steps described below unless otherwise noted.

R21 is a mouse monoclonal antibody directed against amino acids 203-216 of human sACfl protein[14]. The primary antibody (3 mg/ml-1, 1:500) was applied for 25 minutes in a buffered Primary Antibody Diluent (AR9352) from Leica Microsystems. Following this step the sections were treated by a post primary AP step for 20 minutes for signal amplification as part of the procedure detailed in the Leica Microsystems Bond Polymer AP Red Detection kit (part number DS9305). The amplification polymer was then added for 30 minutes followed by two washes in wash buffer and one in deionized water. Finally, the mixed red substrate was applied for 10 minutes followed by an additional 10 minutes with new substrate, three washes in deionized water only, and, finally, mounting with coverslip.

When blocking peptide was used, the antibody was pre-diluted in Bond Primary Antibody Diluent with and without blocking peptide (100 molar excess) and rocked at room temperature overnight. These pre-diluted solutions were used for immunostaining as above.

When R21 was immunostained alone, hematoxylin (part of Bond Polymer Define Detection kit) co-stain was used to highlight the nuclei. The stain was incubated on the slide for 5 minutes followed by one wash in 70% alcohol, three washes in 100% alcohol, two washes in Citrasolv (Fisherbrand 22-143975), and mounting with coverslip.

For co-staining of R21 stained sections with phosphory-lated CREB antibody (1:500) antibody, the sample was pre-treated by two washes of Leica Microsystems HIER1 (part number AR9961), followed by HIER1 pretreatment for 30 minutes at 100° C., and then HIER1 pretreatment for 12 minutes at ambient temperature. Before immunostaining, the sections were blocked using the Dako Dual Endogenous Enzyme Block (part number 52003) for 5 minutes.

The primary antibody was applied for 30 minutes in Bond Primary Antibody Diluent. Following this step the sections were treated with a post primary AP step for 20 minutes for signal amplification as part of the procedure detailed in the Leica Microsystems Bond Polymer AP Red Detection kit (part number DS9305). The amplification polymer was then added for 30 minutes followed by three washes. Finally the Alkaline Phosphotase Substrate kit III Vector (part number SK-5300) was applied for 10 minutes followed by an additional 10 minutes with new substrate, three washes, and, finally, mounting with coverslip.

For co-staining with Melan-A (1:50), PGP9.5 (1:2500), CD1a (1:20), CD3 (1:100), CD20 (1:200), CD56 (1:50), CD68 (1:300), and CD123 (1:50), following staining with R21, the samples were blocked using the Peroxidase Block (part of the Leica Biosystems Bond Polymer Define Detection kit, part number DS9713) for 5 minutes. Sections were then pretreated in HIER2 for 20 or 30 minutes and washed as above, depending on the antibody, as per manufacturer's instructions. This was followed by three washes at 35° C. and one wash at ambient temperature.

The primary antibody was applied for 25 minutes in Bond Primary Antibody Diluent followed by three washes. Following this step the sections were treated with a post primary step for 15 minutes for signal amplification as part of the procedure detailed in the Leica Microsystems Bond Polymer Define Detection kit (part number DS9713) followed by three washes in wash buffer. The amplification polymer was then added for 30 minutes followed by two washes in wash buffer and one in deionized water. Finally, the Mixed Diaminoben-zidine (DAB) Define was applied for 10 minutes. Counter-staining was accomplished by adding hematoxylin for 5 minutes.

Cell Culture and Immunocytochemistry

MDCK cells were cultured in DMEM+10% fetal calf serum and grown to confluence on glass coverslips. Confluent cultures were fed daily over 1 week to allow complete differentiation of the cells. At this point, some coverslips were immunostained while others were trypsinized and split on fresh coverslips at a lower density to induce proliferation. These cells were immunostained within 24 hours of trypsinization. For immunostaining, coverslips were washed in phosphate-buffered saline, fixed for 30 minutes in 4% paraformaldehyde, and permeabilized in 0.1% Triton X-100, and then blocked in 2% bovine serum albumin for at least 1 hour. Cells were stained with anti-sAC rabbit polyclonal antibody overnight in 2% BSA/0.01% Triton X-100, washed three times over 10 minutes in 2% BSA/0.01% Triton X-100, stained for 1 hour at room temperature with goat-anti-rabbit Alexa Fluor-488 (Molecular Probes, Eugene, Oreg.), treated with DAPI for 5 minutes, and then washed and mounted with gelvatol/DABCO (Sigma, St Louis, Mo.).

Example 1

Establishing sAC Location Relevant to Disease

Formalin fixed-, paraffin embedded-human skin from patients with psoriasis, squamous cell carcinoma, verruca vulgaris, and human skin controls were immunostained with multiple monoclonal antibodies, which recognize soluble adenylyl cyclase (R21, R33, R40, R37). Slides were visualized on a standard pathology microscope and localization of staining was confirmed by a board certified dermatopathologist.

Figure 1:
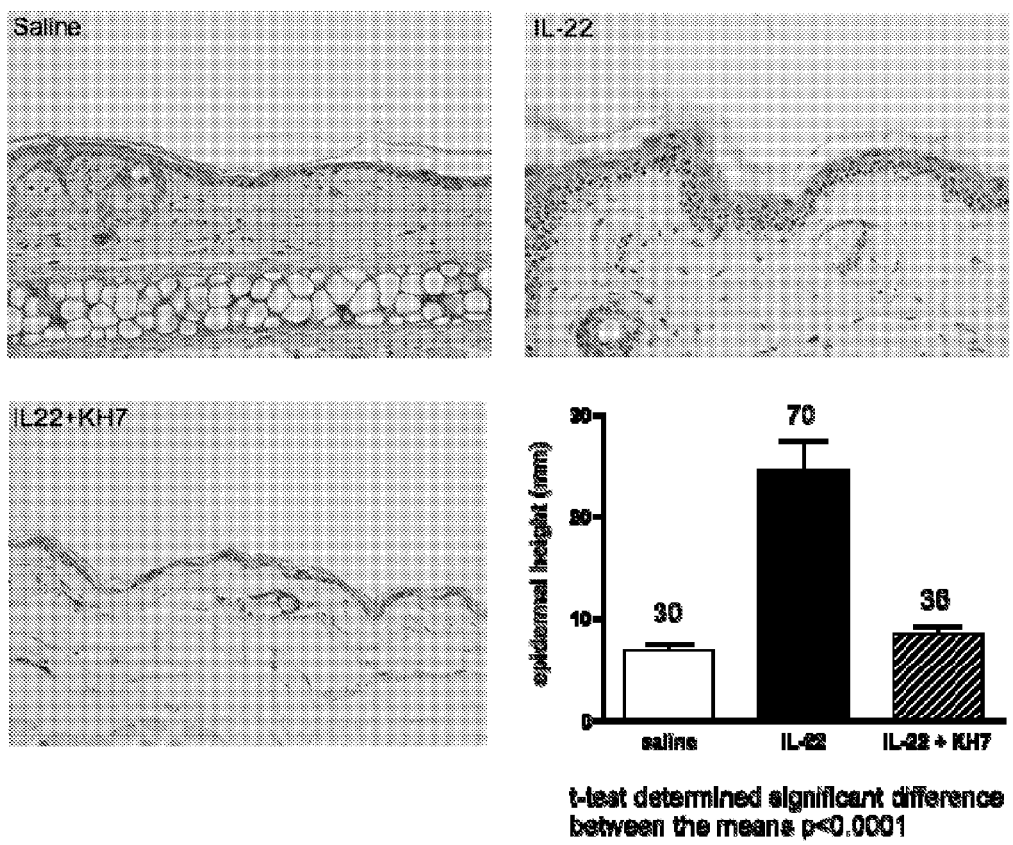
FIG. 1 Tissue sections stained with H/E of C57B1/6 mouse ears following injection with saline, IL-22 and IL-22+KH7 (a sAc inhibitor). Slides were visualized on a standard pathology microscope. Bar graph in lower right corner represents the average±SEM thickness of epidermis in each of three conditions listed in the previous sentence. a student t test was performed with p value listed. As demonstrated in the sections and the bar graph, inclusion of sAC inhibitor completely blocked IL-22-induced acanthosis and recruitment of immunocytes (ie T cells).
Figure 2:
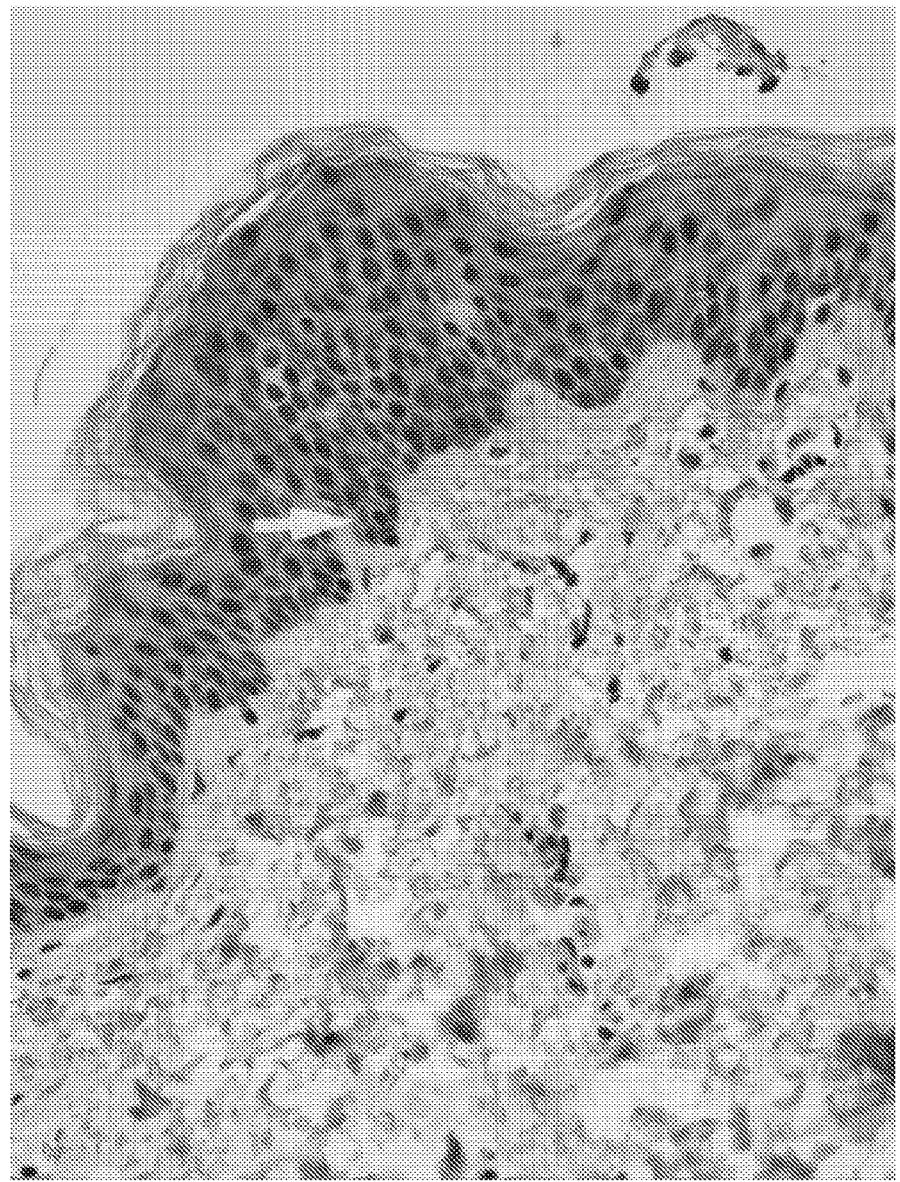
FIG. 2 Immunostaining of normal human skin with R21 monoclonal antibody. Slides were visualized on a standard pathology microscope. This image is 40× magnification. Staining was diffusively cytoplasmic with occasional nuclear staining FIG. 3 Immunostaining of normal human skin with R21 monoclonal antibody. Slides were visualized on a standard pathology microscope. This image is 40× magnification. Staining was diffusively cytoplasmic with occasional nuclear staining FIG. 4 Immunostaining of psoriatic human skin with R21 monoclonal antibody. Slides were visualized on a standard pathology microscope. This image is 20× magnification. Unlike normal skin, staining was enhanced in the nucleus of many keratinocytes and was reduced in the cytoplasm.
Figure 3:
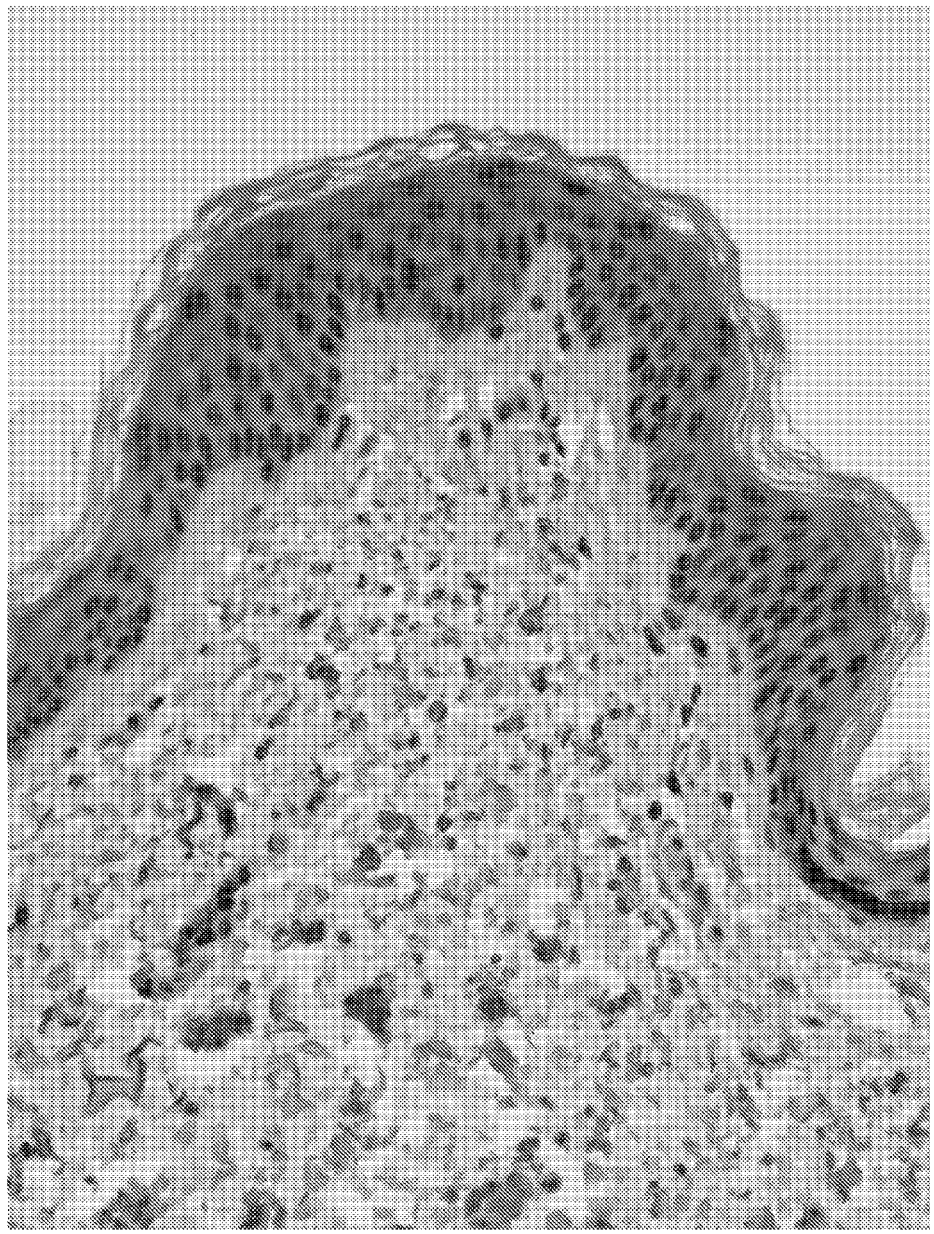
Figure 4:
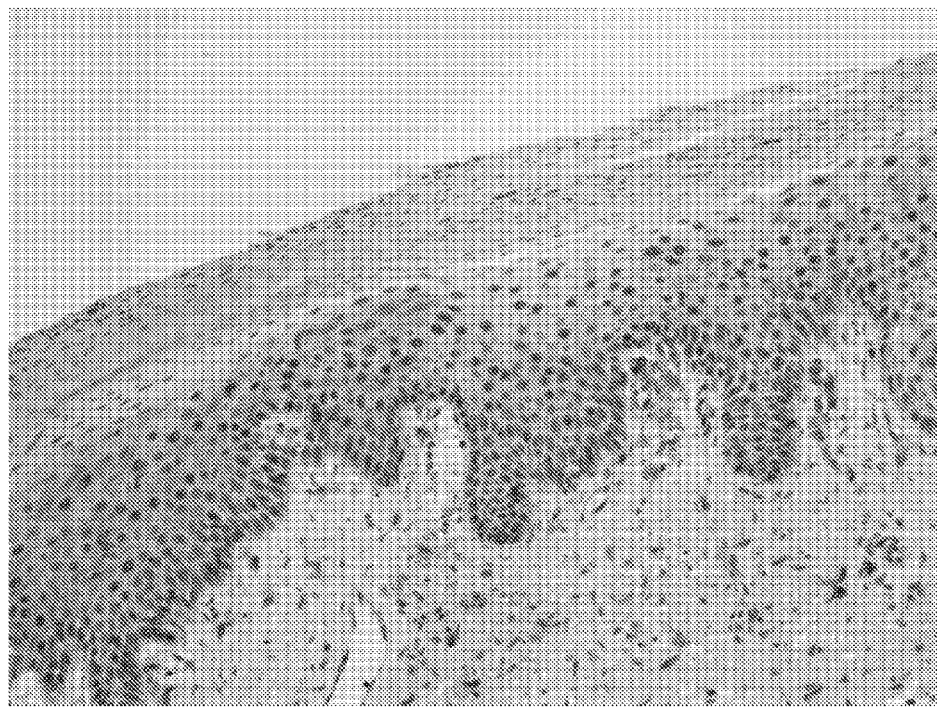
Figure 5:
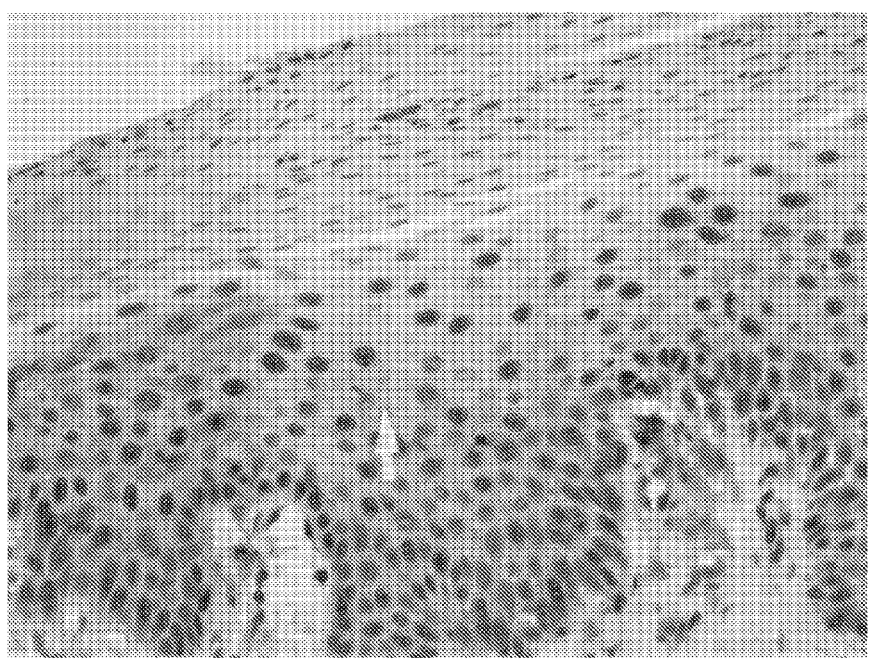
FIG. 5 Immunostaining of psoriatic human skin with R21 monoclonal antibody. Slides were visualized on a standard pathology microscope. This image is 40× magnification. Unlike normal skin, staining was enhanced in the nucleus of many keratinocytes and was reduced in the cytoplasm.
Figure 6:
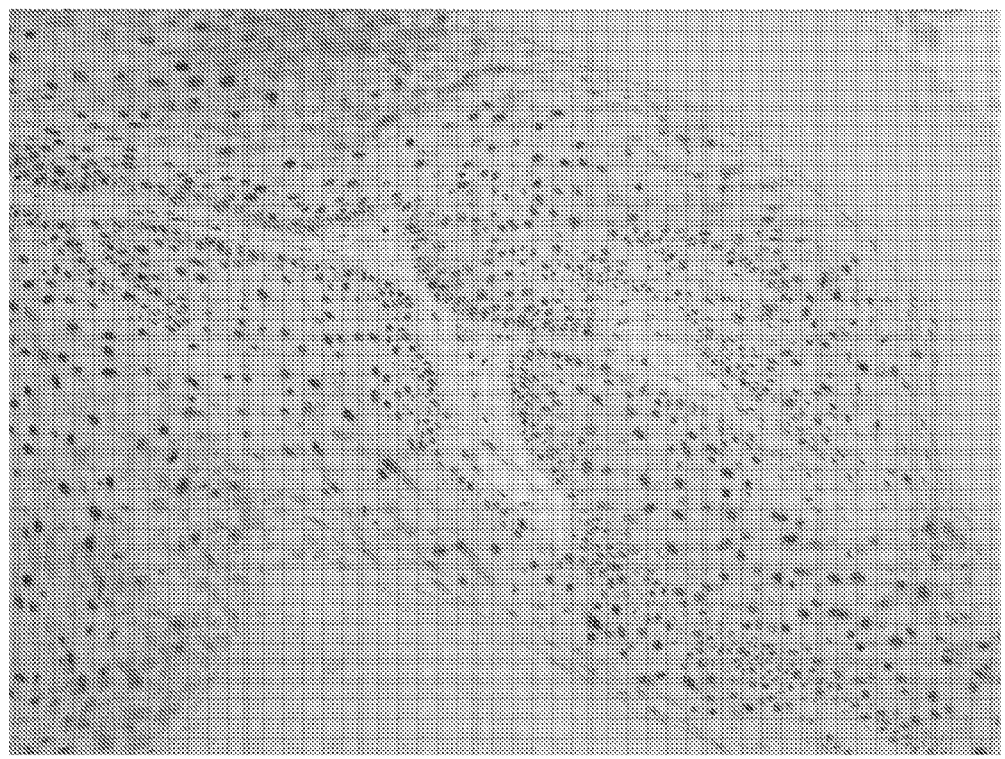
FIG. 6 Immunostaining of verruca vulgaris in human skin with R21 monoclonal antibody. Slides were visualized on a standard pathology microscope. This image is 20× magnification. Unlike normal skin, staining was enhanced in the nucleus of many keratinocytes and was reduced in the cytoplasm.
Figure 7:
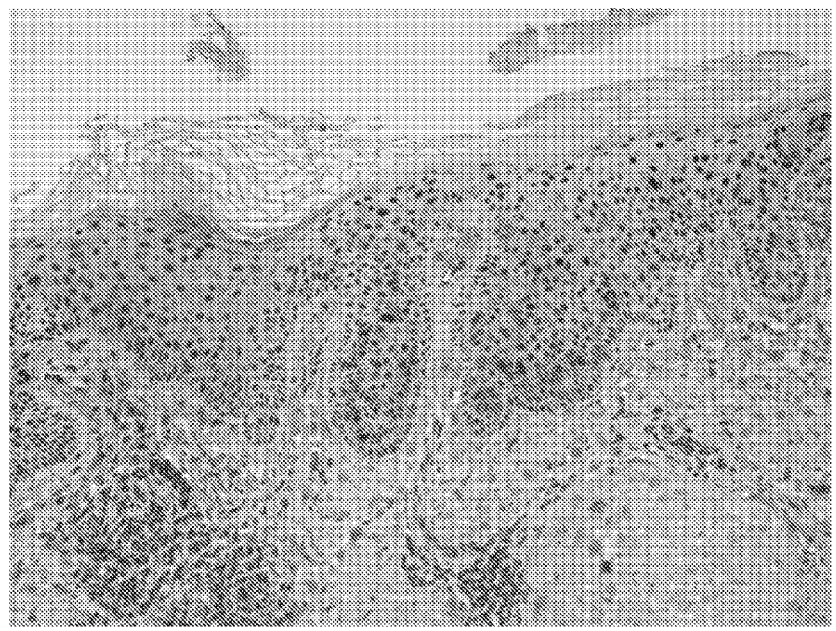
FIG. 7 Immunostaining of squamous cell carcinoma in situ in human skin with R21 monoclonal antibody. Slides were visualized on a standard pathology microscope. This image is 20× magnification. Unlike normal skin, staining was enhanced in the nucleus of many keratinocytes and was reduced in the cytoplasm.
Figure 8:
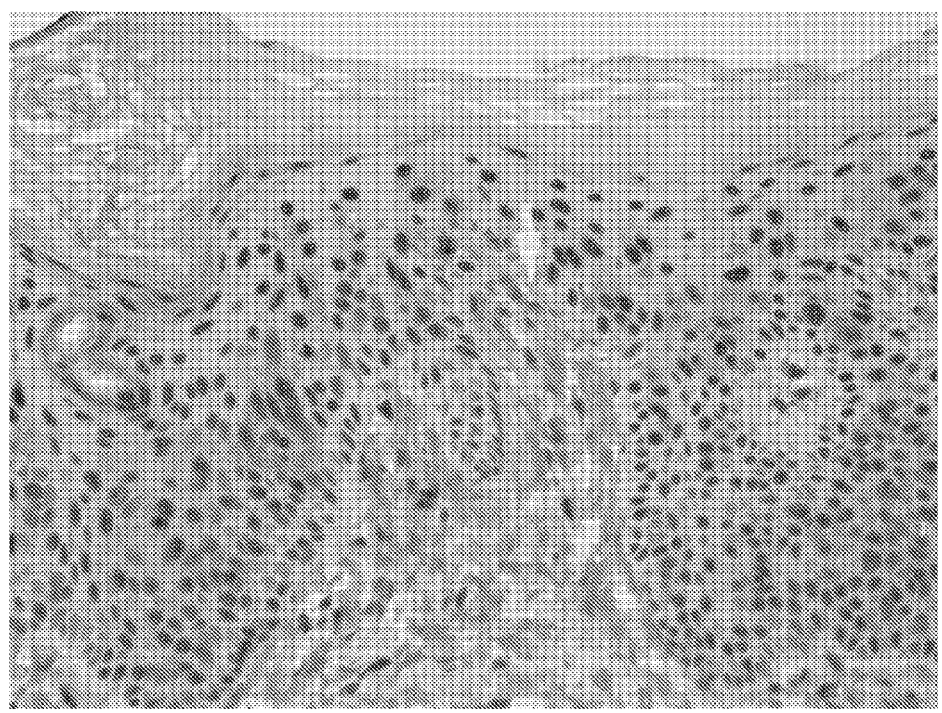
FIG. 8 Immunostaining of squamous cell carcinoma in situ in human skin with R21 monoclonal antibody. Slides were visualized on a standard pathology microscope. This image is 40× magnification. Unlike normal skin, staining was enhanced in the nucleus of many keratinocytes and was reduced in the cytoplasm.
Figure 9:
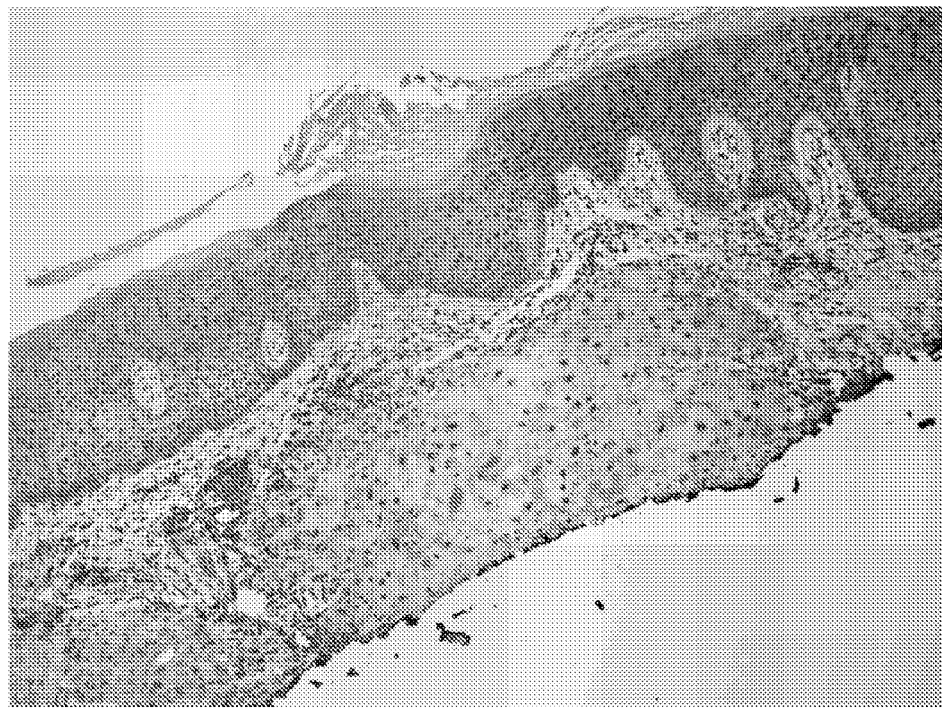
FIG. 9 Immunostaining of squamous cell carcinoma in human skin with R21 monoclonal antibody. Slides were visualized on a standard pathology microscope. This image is 20× magnification. Unlike normal skin, staining was enhanced in the nucleus of many keratinocytes and was reduced in the cytoplasm.
Figure 10:
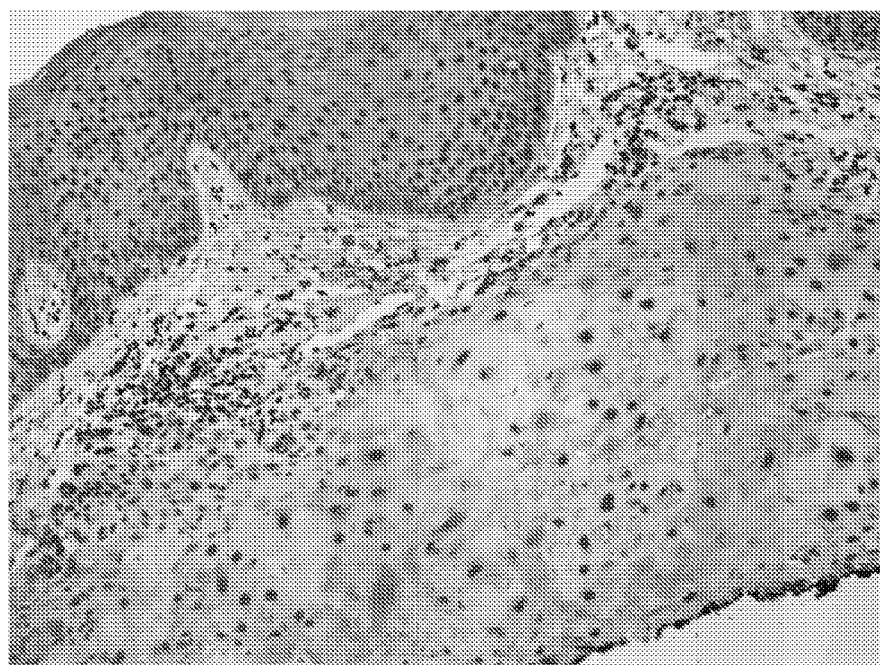
FIG. 10 Immunostaining of squamous cell carcinoma in human skin with R21 monoclonal antibody. Slides were visualized on a standard pathology microscope. This image is 40× magnification. Unlike normal skin, staining was enhanced in the nucleus of many keratinocytes and was reduced in the cytoplasm.

Immunostaining of normal (FIGS. 2 and 3) and psoriatic (FIGS. 4 and 5) human skin established that while in normal skin sAC was present in both the cytoplasm and the nucleus, in acanthotic skin diseases including psoriasis (FIGS. 4 and 5), verruca vulgaris (FIG. 6), squamous cell carcinoma in situ (FIGS. 7 and 8), and squamous cell carcinoma (SCC) (FIGS. 9 and 10), sAC was predominantly, if not exclusively, nuclear. Psoriatic acanthosis and parakeratosis occur when kerati-nocytes exit a differentiation program and enter a proliferative state. Therefore sAC translocation in and out of the nucleus and concomitant changes in cAMP-mediated gene expression have a role in psoriatic keratinocyte proliferation.

Example 2 sAc Immunostaining in Normal Human Skin

Using a previously described mouse monoclonal antibody against human sAC protein[12,14], sAC expression in normal human skin was examined. sAC was present in multiple cell types within both epidermis and dermis (FIG. 12a-f). All specific staining was absent if primary antibody was either incubated with blocking peptide (FIG. 12c) or omitted. In the epidermis, sAC was strongly expressed in keratinocytes (FIG. 12b). Staining appeared evenly distributed throughout the cell, without specific localization. There were occasional cells with nuclear staining, but these cells represented a minority of the total keratinocytes. sAC was absent in the cornified cell layer. sAC protein was also present in melanocytes as confirmed by costaining with Melan-A (FIG. 12d). sAC was present in a variety of mononuclear cells in the dermis (FIG. 12b). Co-staining with different markers, such as CD3, CD20, CD1a, and CD56, established that these cells consisted of T-cells, macrophages, and dendritic cells. sAC was also present in eccrine duct cells (FIG. 12e). In addition, we found sAC protein in cutaneous nerve axons as confirmed by co-staining with PGP9.5 (FIG. 12f).

Example 3 sAC Immunostaining in Common Viral Infections of the Epidermis

Figure 13:
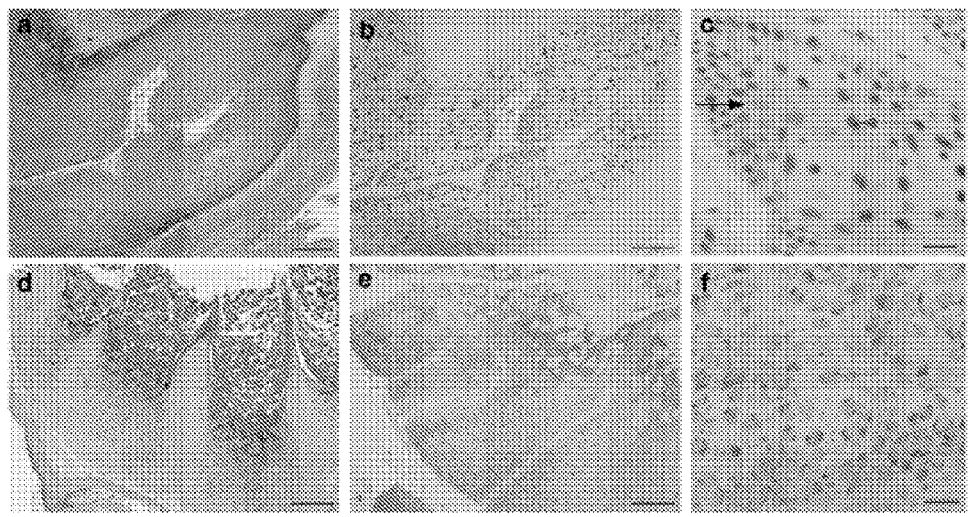
FIG. 13 Immunostaining of sAC in viral infections of the epidermis. (a) Hematoxylin (blue) and eosin (red) staining of a verruca vulgaris skin lesion. (b) Verruca vulgaris skin lesion immunostained with R21 (red) and hematoxylin (blue). (c) Verruca vulgaris skin lesion immunostained with R21 (red) and hematoxylin (blue). The black arrow demonstrates a nucleus negative for sAC. The gray arrow demonstrates a nucleus positive for sAC. (d) Hematoxylin (blue) and eosin (red) staining of a molluscum contagiosum skin lesion. (e) Molluscum contagiosum skin lesion immunostained with R21 (red) and hematoxylin (blue). (f) Molluscum contagiosum skin lesion immunostained with R21 (red) and hematoxylin (blue). Bars=100 µm (a, b, d, e) and 10 µm (c, f).

In most lesions of verruca vulgaris (FIG. 13a-c and Table 1), sAC cytoplasmic staining was significantly reduced as compared with normal epidermis (FIG. 12b), and instead sAC was predominately nuclear throughout the lesion. As in normal epidermis, staining was mainly undetectable in the cornified layer. sAC was not exclusively present in the nucleus. While some cells had strong nuclear staining (FIG. 13c, gray arrow), other nuclei had no sAC staining (FIG. 13c, black arrow). In contrast to HPV-induced skin lesions, molluscum contagiosum virus (MCV) infection did not induce a predominance of sAC nuclear staining (FIG. 13d-f and Table 1). In fact, rarely could a nucleus positive for sAC staining be observed. Instead, sAC staining was granular in quality and perinuclear in localization (FIG. 13f).

TABLE 1

Degree of nuclear sAC staining in examples of keratinocyte hyperproliferative skin disease

| | Expression pattern | | |
|---|---|---|---|
| | + | +/− | − |
| Verruca vulgaris | 6 | 0 | 3 |
| Molluscum contagiosum | 0 | 0 | 7 |
| Seborrheic keratosis | 6 | 1 | 3 |
| Epidermolytic hyperkeratosis | 0 | 0 | 4 |
| Acanthosis nigricans | 0 | 3 | 2 |
| Actinic keratosis | 4 | 1 | 0 |
| Bowenoid papulosis with high-grade dysplasia, +HPV in situ | 1 | 3 | 7 |
| Squamous cell carcinoma in situ, no dermal involvement, sun-exposed sites | 9 | 1 | 3 |
| Squamous cell carcinoma, invasion of dermis, both sun-exposed and non-exposed sites | 3 | 1 | 2 |
| Basal cell carcinoma | 0 | 0 | 10 |
| Pityriasis rubra pilaris | 0 | 1 | 2 |
| Psoriasis vulgaris | 5 | 5 | 0 |
| Psoriasis pustular | 3 | 0 | 0 |
| Psoriasis guttate | 4 | 0 | 0 |

Abbreviation: sAC, soluble adenylyl cyclase.

−: Approximately 10% of keratinocytes have nuclei positive for sAC and sAC staining is strongly cytoplasmic (equivalent to normal skin); +/−: 10-70% of keratinocytes have nuclei positive for sAC and decreased cytoplasmic sAC staining in keratinocytes with sAC nuclear staining; +: >70% of keratinocytes have nuclei positive for sAC, with barely detectable cytoplasmic sAC staining Example 4

In Vitro Epithelial Cell Model of Differentiation

Figure 14:
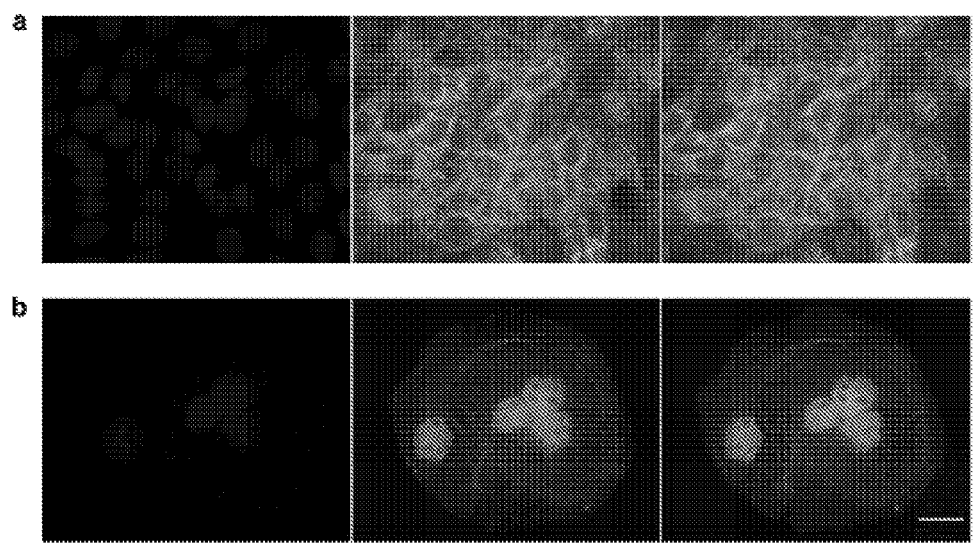
FIG. 14 sAC is present in the nucleus when epithelial cells are proliferating and not when epithelial cells are differentiating. (a) Differentiated MDCK cells stained with DAPI (left), anti-N-term sAC antibody (center), and overlay of DAPI and anti-N-term (right). (b) Proliferating undifferentiated MDCK cells stained with DAPI (left), anti-N-term sAC antibody (center), and overlay of DAPI and anti-N-term (right). Bar=10 µm.

Madin-Darby canine kidney (MDCK) cells (FIG. 14), Caco-2 human colonic cells, and human retinal pigment epithelial cells represent three of the best-characterized models of epithelial differentiation[20]. When these cell lines are grown to confluence, cellular division stops and cells develop tight junctions and other markers of epithelial differentiation. Eventually, these cells form the functional sheets of polarized epithelial cells. Once fully differentiated, sAC staining in the epithelial-like cells was exclusively within the cytoplasm of MDCK (FIG. 14a, middle panel), Caco-2, and retinal pigment epithelial cells. A key feature of these cell models is that differentiation is not permanent; simple removal of cellular contacts induces the cells to de-differentiate and resume proliferation. There are two established methods for disrupting cell-to-cell contacts of the epithelial sheets: clearing a line of cells by scraping with a metal spatula (sometimes referred to as wounding) or by simple trypsinization. After wounding or trypsinization (FIG. 14b), sAC nuclear staining returned in MDCK (FIG. 14b, middle panel), Caco-2, and retinal pigment epithelial cells.

Example 5 sAC Immunostaining in UV-Induced Keratinocyte Neoplasms

Figure 17:
FIG. 17 Immunostaining of sAC in seborrheic keratosis. a, Hematoxylin (red) and eosin (blue) staining of seborrheic keratosis. b, Seborrheic keratosis immunostained with R21 (red) and hematoxylin (blue). c, Seborrheic keratosis immunostained with R21 (red) and hematoxylin (blue). Scale bars=50 µm (a,b) and 10 µm (c).

UV radiation is capable of inducing both benign and malignant neoplasms of the epidermis. Seborrheic keratoses are benign neoplasms. In the majority of seborrheic keratoses examined (FIG. 17 and Table 1), sAC staining was predominately nuclear, with a relatively decreased level of cytoplasmic staining as compared with normal skin (FIG. 12b).

Figure 15:
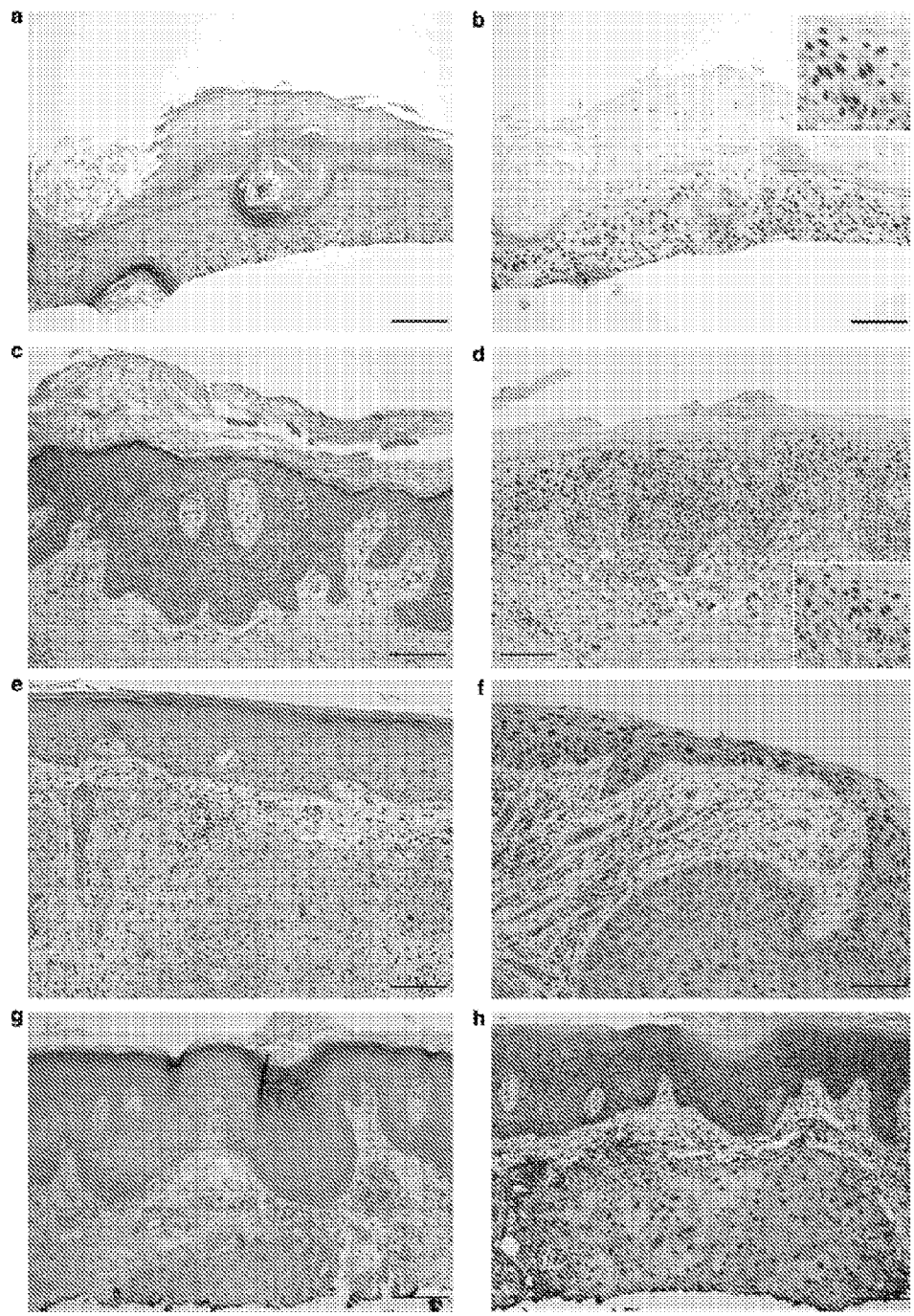
FIG. 15 Immunostaining of sAC in AK and SCC. (a) Hematoxylin (red) and eosin (blue) staining of AK. (b) AK immunostained with R21 (red) and hematoxylin (blue); inset, magnified view of the area in panel b. (c) Hematoxylin (red) and eosin (blue) staining of SCCIS. (d) SCCIS immunostained with R21 (red) and hematoxylin (blue); inset, magnified view of the area in panel d. (e) Hematoxylin (red) and eosin (blue) staining of SCC. (f) SCC immunostained with R21 (red) and hematoxylin (blue). (g) Hematoxylin (red) and eosin (blue) staining of SCC. (h) SCC immunostained with R21 (red) and hematoxylin (blue). Bars=50 µm.

Actinic keratosis (AK), SCC in situ (SCCIS), and invasive SCC can be considered as a continuum of increasing pathogenecity. All three neoplasms occur secondary to UV-induced DNA damage and in most cases are typified by mutations in p53[21]. In AKs, sAC staining was enriched in the nucleus and significantly decreased in the cytoplasm (FIGS. 15a and b, inset and Table 1). Nearly all SCCIS cases examined had a similar sAC staining pattern to AKs; that is, sAC was enriched in the nucleus and was relatively decreased in the cytoplasm as compared with normal skin (FIGS. 15c and d, inset and Table 1). sAC staining in invasive SCC revealed a more mosaic pattern. Approximately 50% of SCC samples examined (Table 1), regardless of subtype, had strong nuclear sAC staining in the SCCIS component, but no nuclear sAC staining in the invasive component (FIGS. 15e and f). In fact, in some of these SCC cases the invasive component was devoid of all sAC staining. The remaining SCC cases retained a predominant nuclear sAC staining pattern, with a relatively decreased cytoplasmic staining intensity (FIGS. 15g and h, and Table 1).

Figure 18:
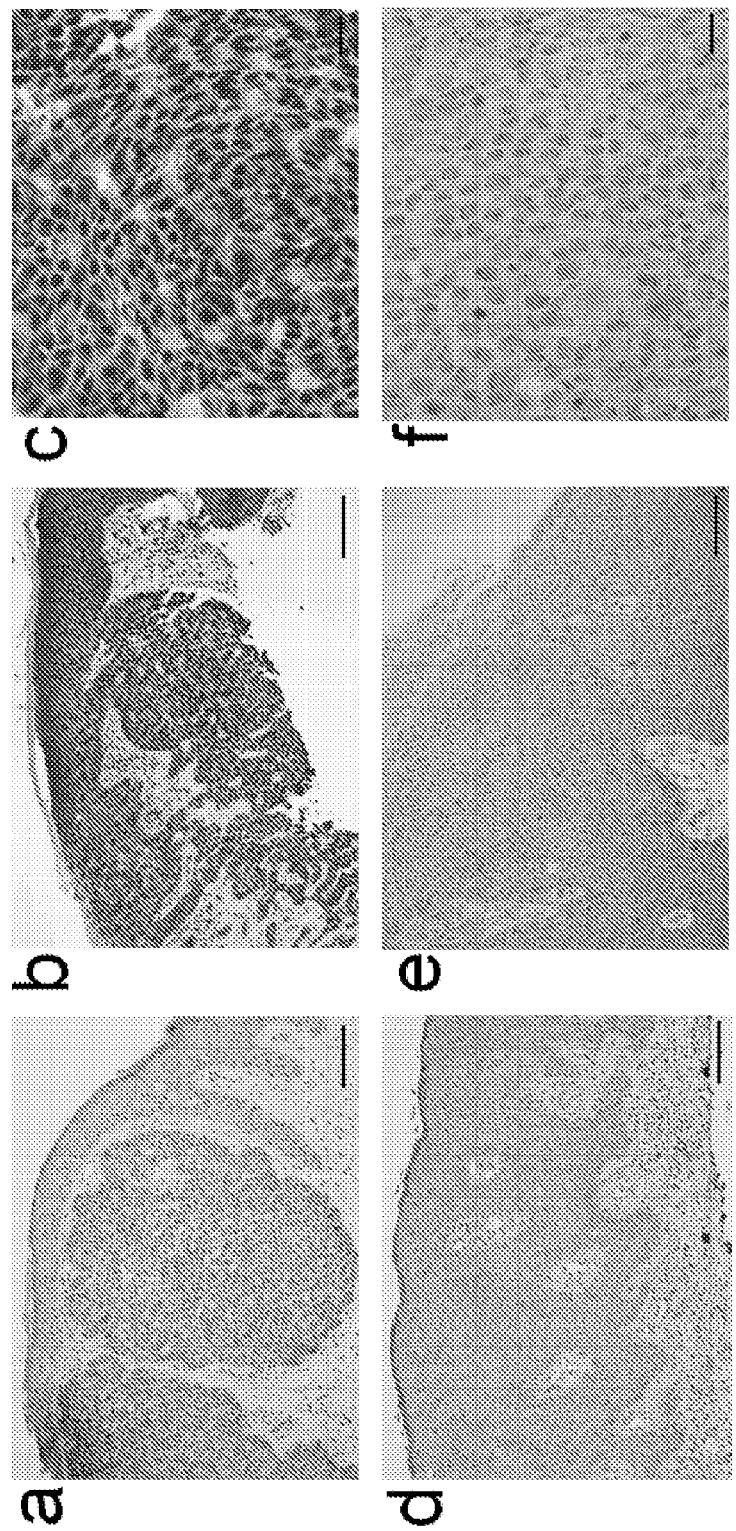
FIG. 18 Immunostaining of sAC in bowenoid papulosis and basal cell carcinoma. a, Hematoxylin (red) and eosin (blue) staining of basal cell carcinoma. b, Basal cell carcinoma immunostained with R21 (red) and hematoxylin (blue). c, Basal cell carcinoma immunostained with R21 (red) and hematoxylin (blue). d, Hematoxylin (red) and eosin (blue) staining of bowenoid papulosis. e, Bowenoidpapulosis immunostained with R21 (red) and hematoxylin (blue). f, Bowenoid papulosis immunostained with R21 (red) and hematoxylin (blue). Scale bars=50 µm (a,b,d,e) and 10 µm (c,f).

Compared with SCC, basal cell carcinoma demonstrated a very different sAC immunostaining pattern. sAC staining was virtually absent from all nuclei; the frequency of nuclear staining was equivalent to the frequency in normal skin. sAC staining in BCC was intense and diffusely cytosolic, and this pattern was identical among all basal cells carcinomas analyzed regardless of pathologic subtype (FIG. 18a-c and Table 1). Of all the epidermal diseases examined, sAC localization in BCC most closely resembled that in normal skin.

Example 6 sAC Immunostaining in Virally Induced Malignant Neoplasms

Although the vast majority of HPV infections develop into benign growths, a few HPV subtypes, namely 16, 18, 31, and 33, cause high-grade squamous proliferative lesions in the skin ranging from bowenoid papulosis to frank carcinoma. Although these neoplasms are caused by HPV infection, sAC localization in high-risk HPV infections did not match sAC localization in low-risk HPV infections (FIG. 13a-c). Instead, sAC localization was absent from the nucleus and present in a perinuclear granular staining pattern (FIG. 18d-f).

Example 7 sAC Immunostaining in Benign Inflammatory Proliferations of the Epidermis

A consistent sAC staining pattern in a variety of human psoriasis cases, including at least five examples of guttate, plaque-type, and pustular psoriasis (Table 1) was observed. Among all forms of psoriasis, within the area of epidermal thickening, sAC staining changed from predominately cytoplasmic (FIG. 12b) to a distribution where sAC protein was almost exclusively nuclear (FIG. 16b, inset, white arrow). sAC was not present in all nuclei (FIG. 16b, inset, black arrow), nor did sAC expression extend into the area of parakeratosis.

Pityriasis rubra pilaris is another disease of keratinocyte proliferation. Although its exact pathophysiological mechanism is not known, it is believed to occur secondary to an antigen-triggered immune response such as streptococcal infection[22]. Unlike psoriasis, sAC staining in pityriasis rubra pilaris biopsies was predominately cytoplasmic, with little to no increase in nuclear staining (Table 1).

Example 8

In Psoriasis, Nuclear sAC is Associated with Activated cAMP Effector Proteins cAMP-dependent gene expression, mediated by the transcription factor CREB, is known to occur in psoriatic keratinocytes[23], and nuclear sAC is capable of activating CREB by inducing a PKA-dependent phosphorylation[12]. Staining psoriasis skin samples with an antibody that recognizes the phosphorylated (ie, activated) form of CREB demonstrated that a large number of keratinocyte nuclei were positive for phosphoCREB, and that the majority of keratinocytes that contain high levels of active CREB also contain high levels of nuclear sAC (FIG. 16c).

Example 9

In Vivo Experiment

To address the role of sAC in keratinocyte proliferation we studied IL-22-induced psoriasis pathogenesis as a model system. IL-22 induced a rise in cAMP within keratinocytes in culture. This cAMP rise was inhibited by KH7 (a specific inhibitor of sAC). These data suggest that previously published in vivo IL-22-induced acanthosis and other psoriasis pathogenic events[18] might also be sensitive to sAC inhibition.

We tested this hypothesis by injecting C57B1/6 mouse ears with IL-22[24] and IL-22+KH7 or by injecting IL22 and treating topically with vehicle or KH7. sAC inhibition completely blocked IL-22-induced acanthosis and parakeratosis, implying that sAC activity is essential for IL-22-dependent psoriasis pathogenesis.

Methods used for Data Acquisition

IL-22 protein was purchased from Preprotech and reconstituted in sterile water as per the manufacturer's instructions. Concentrated IL-22 was diluted to a working concentration of 500 ng/20 µL in sterile saline alone, or with KH7 at 100 µM. These solutions were prepared fresh each day they were used. C57B1/6 mice greater than 2 months in age, kept under a normal light/dark cycle, and fed normal chow were injected subcutaneously in their left ear with 20 µL of IL-22 alone and in their right ear with 20 µL of IL-22+KH7 every other day for two weeks, or were injected subcutaneously in their left and right ear with 20 µL of IL-22 and then treated topically (54) following each injection with vehicle on the left ear and KH7 on the right ear every other day for two weeks. As a control C57B1/6 mice were injected with 20 µL of IL-22 in their left ear and 20 µL of sterile saline alone in their right ear every other day for two weeks. After two weeks the ears were removed, formalin fixed, paraffin embedded, sectioned, and stained with simple hematoxylin and eosin. Epidermal height was measured from the bottom of the basal cell layer to the top of the granular cell layer using a microscope and a micrometer. Three to four measurements were taken along the ear and multiple sections were measured for each condition. In addition, the total number of acanthotic ear sections were recorded as an indication of the distribution of acanthosis.

Result: In normal skin, sAC was present in the cytoplasm and the nucleus of epidermal keratinocytes; whereas, in psoriatic keratinocytes, sAC was enriched in the nucleus and nearly absent in the cytoplasm. This was also true in other acanthotic skin diseases (e.g., verruca vulgaris and SCC). Finally, IL-22 treatment of mouse epidermis led to acanthosis and parakeratosis similar to psoriatic lesions; and inclusion of KH7, a sAC inhibitor, completely blocked these effects.

Example 10

Small Molecule sAC Inhibitors

TABLE 2

| Structure | Name |
| --- | --- |

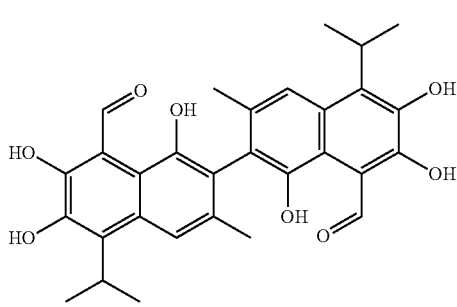 [SMILES: Cc1cc2c(C(C)C)c(O)c(O)c(C=O)c2c(O)c1-c1c(C)cc2c(C(C)C)c(O)c(O)c(C=O)c2c1O]

Gossypol

TABLE 2-continued
| Structure | Name |
|---|---|
| 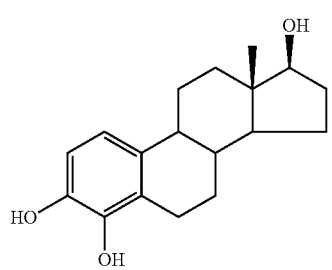 [SMILES: C[C@]12CCC3c4ccc(O)c(O)c4CCC3C1CC[C@@H]2O] | 4-hydroxyestradiol |
| 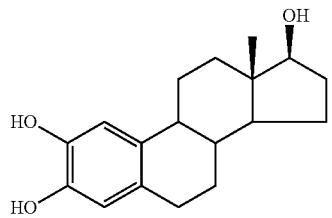 [SMILES: C[C@]12CCC3c4cc(O)c(O)cc4CCC3C1CC[C@@H]2O] | 2-hydroxyestradiol |
| 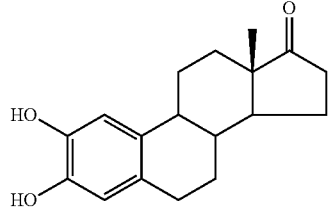 [SMILES: C[C@]12CCC3c4cc(O)c(O)cc4CCC3C1CCC2=O] | 2-hydroxyestrone |
| 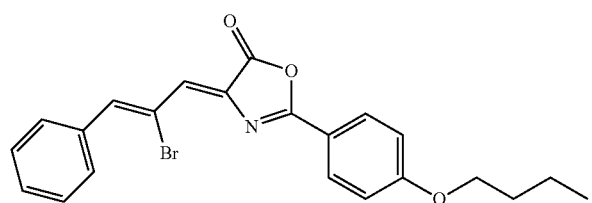 [SMILES: CCCCOc1ccc(C2=N/C(=C\C(Br)=C\c3ccccc3)C(=O)O2)cc1] | KH1 |
| 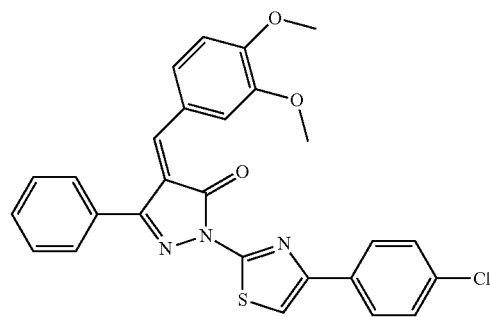 [SMILES: COc1ccc(/C=C2\C(=O)N(c3nc(-c4ccc(Cl)cc4)cs3)N=C2c2ccccc2)cc1OC] | KH2 |
| 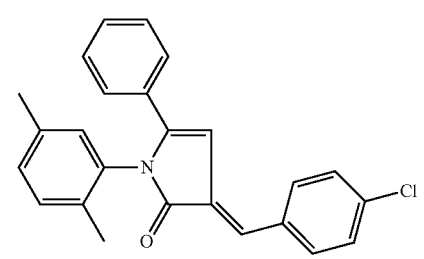 [SMILES: Cc1ccc(C)c(N2C(=O)/C(=C/c3ccc(Cl)cc3)C=C2c2ccccc2)c1] | KH3 |

TABLE 2-continued
| Structure | Name |
|---|---|
| 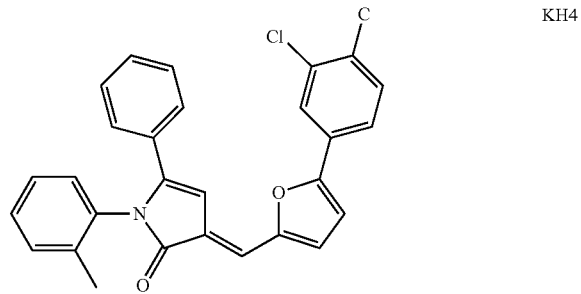 | KH4 |
| 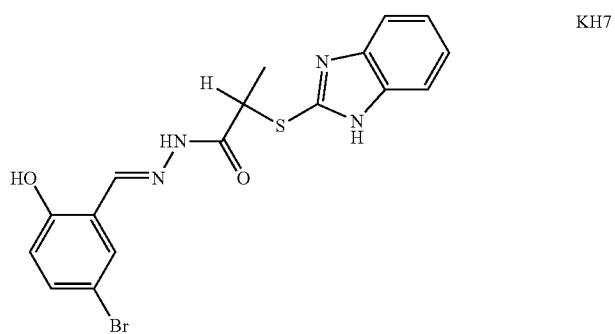 | KH7 |
| 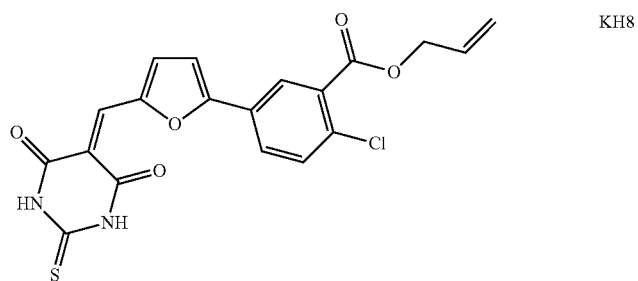 | KH8 |
| 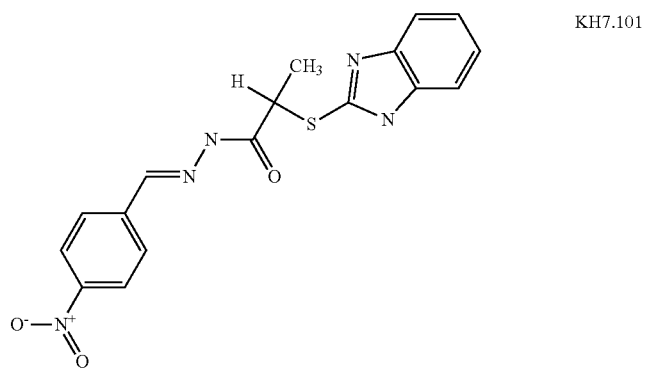 | KH7.101 |
| 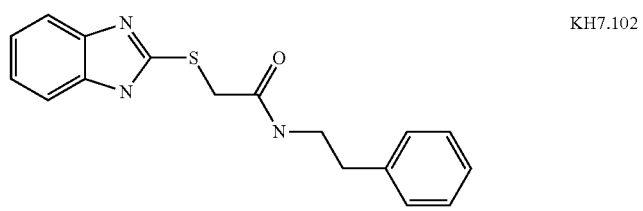 | KH7.102 |

TABLE 2-continued

| Structure | Name |
|---|---|
| 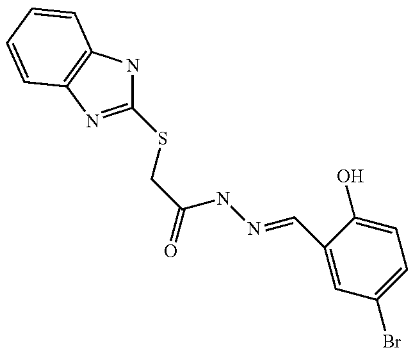 [SMILES: O=C(CSc1nc2ccccc2[nH]1)N/N=C/c1cc(Br)ccc1O] | KH7.103 |
| 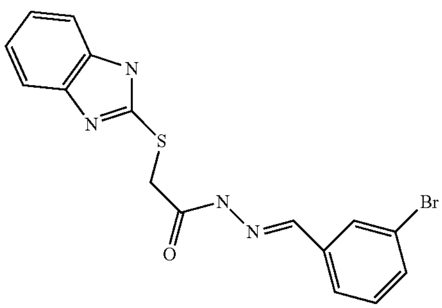 [SMILES: O=C(CSc1nc2ccccc2[nH]1)N/N=C/c1cccc(Br)c1] | KH7.104 |
| 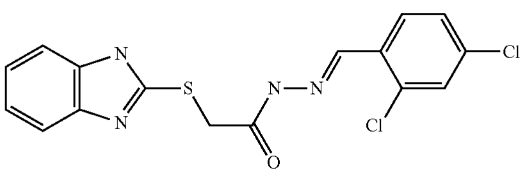 [SMILES: O=C(CSc1nc2ccccc2[nH]1)N/N=C/c1ccc(Cl)cc1Cl] | KH7.105 |
| 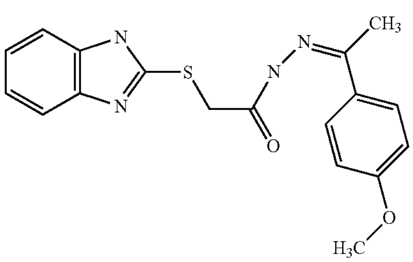 [SMILES: COc1ccc(/C(C)=N\NC(=O)CSc2nc3ccccc3[nH]2)cc1] | KH7.106 |
| 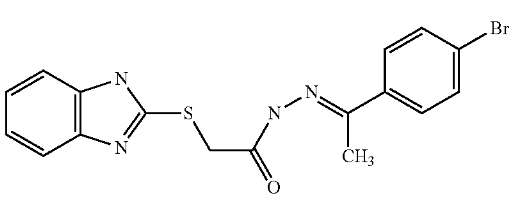 [SMILES: C/C(=N\NC(=O)CSc1nc2ccccc2[nH]1)c1ccc(Br)cc1] | KH7.107 |
| 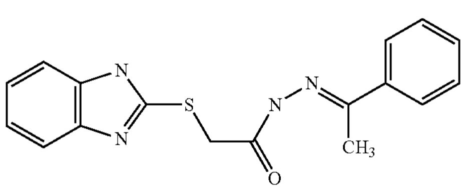 [SMILES: C/C(=N\NC(=O)CSc1nc2ccccc2[nH]1)c1ccccc1] | KH7.108 |

TABLE 2-continued

| Structure | Name |
|---|---|
| 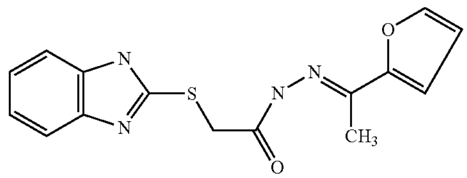 [SMILES: C/C(=N\NC(=O)CSc1nc2ccccc2[nH]1)c1ccco1] | KH7.109 |
| 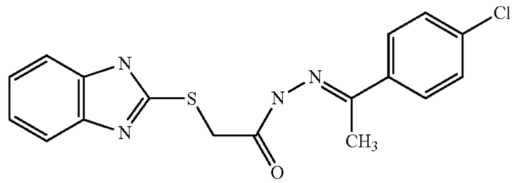 [SMILES: C/C(=N\NC(=O)CSc1nc2ccccc2[nH]1)c1ccc(Cl)cc1] | KH7.110 |
| 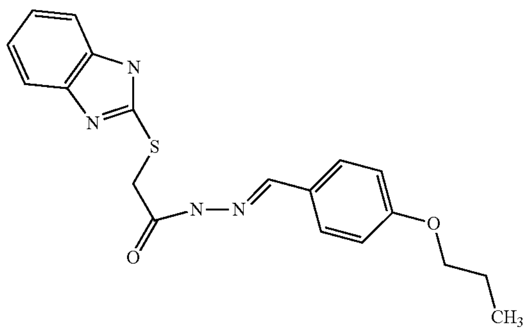 [SMILES: CCCOc1ccc(/C=N/NC(=O)CSc2nc3ccccc3[nH]2)cc1] | KH7.111 |
| 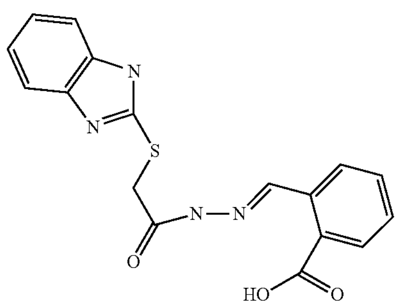 [SMILES: O=C(CSc1nc2ccccc2[nH]1)N/N=C/c1ccccc1C(=O)O] | KH7.112 |
| 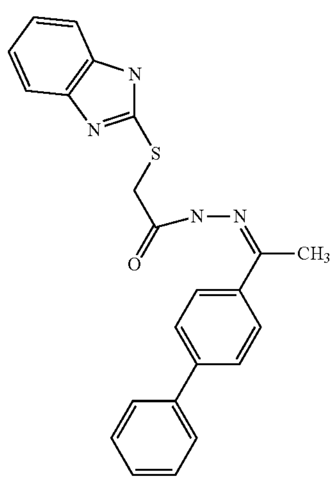 [SMILES: C/C(=N/NC(=O)CSc1nc2ccccc2[nH]1)c1ccc(-c2ccccc2)cc1] | KH7.113 |

TABLE 2-continued

| Structure | Name |
| --- | --- |
| 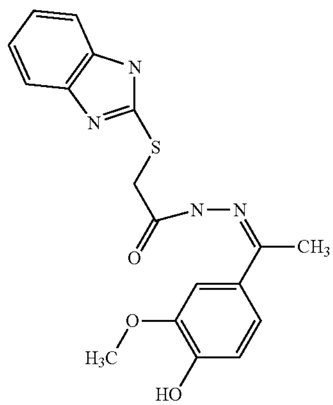 [SMILES: COc1cc(/C(C)=N\NC(=O)CSc2nc3ccccc3[nH]2)ccc1O] | KH7.114 |
| 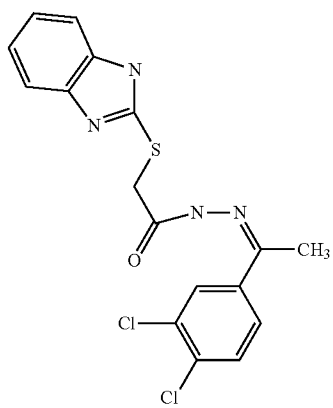 [SMILES: C/C(=N/NC(=O)CSc1nc2ccccc2[nH]1)c1ccc(Cl)c(Cl)c1] | KH7.115 |
| 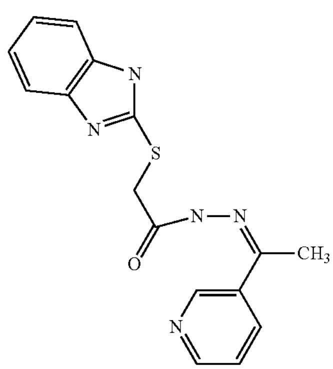 [SMILES: C/C(=N/NC(=O)CSc1nc2ccccc2[nH]1)c1cccnc1] | KH7.116 |
| 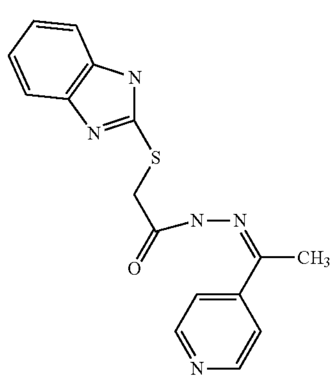 [SMILES: C/C(=N/NC(=O)CSc1nc2ccccc2[nH]1)c1ccncc1] | KH7.117 |

TABLE 2-continued

| Structure | Name |
| --- | --- |
| 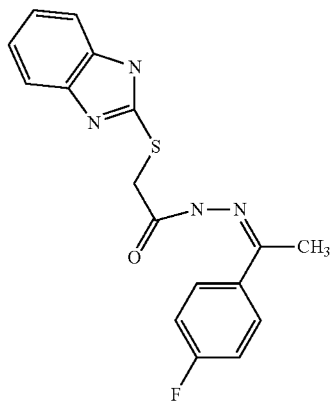 [SMILES: C/C(=N/NC(=O)CSc1nc2ccccc2[nH]1)c1ccc(F)cc1] | KH7.118 |
| 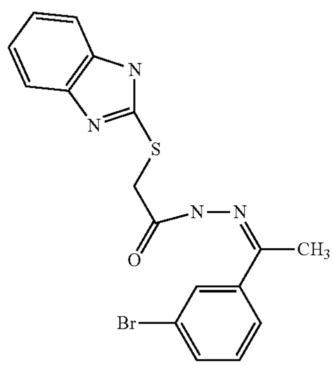 [SMILES: C/C(=N/NC(=O)CSc1nc2ccccc2[nH]1)c1cccc(Br)c1] | KH7.119 |
| 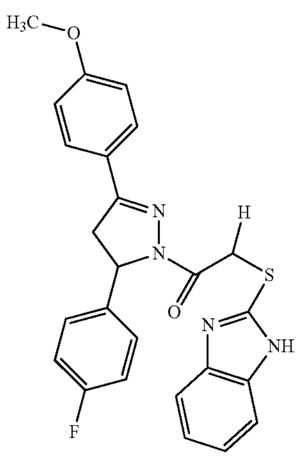 [SMILES: COc1ccc(C2=NN(C(=O)CSc3nc4ccccc4[nH]3)C(c3ccc(F)cc3)C2)cc1] | KH7.120 |
| 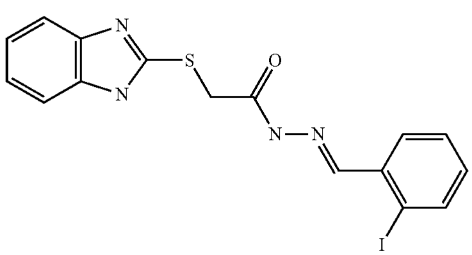 [SMILES: O=C(CSc1nc2ccccc2[nH]1)N/N=C/c1ccccc1I] | KH7.121 |

TABLE 2-continued

| Structure | Name |
|---|---|
| [benzimidazol-2-ylthio-CH2-C(O)-NH-N=CH-C6H4-NO2 (para)] | KH7.122 |
| [benzimidazol-2-ylthio-CH2-C(O)-NH-N=CH-(pyridin-3-yl)] | KH7.123 |
| [benzimidazol-2-ylthio-CH2-C(O)-NH-N=CH-(3,5-dimethoxy-4-acetoxyphenyl)] | KH7.124 |
| [benzimidazol-2-ylthio-CH2-C(O)-NH-N=CH-C6H4-O-CH2-C6H5 (para)] | KH7.125 |
| [benzimidazol-2-ylthio-CH2-C(O)-NH-N=CH-(naphthalen-1-yl)] | KH7.126 |

TABLE 2-continued

| Structure | Name |
|---|---|
| 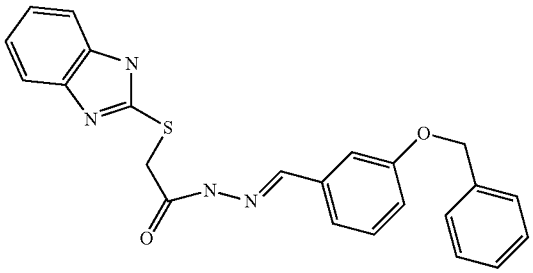 [SMILES: O=C(CSc1nc2ccccc2[nH]1)N/N=C/c1cccc(OCc2ccccc2)c1] | KH7.127 |
| 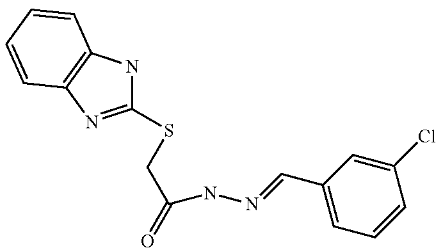 [SMILES: O=C(CSc1nc2ccccc2[nH]1)N/N=C/c1cccc(Cl)c1] | KH7.128 |
| 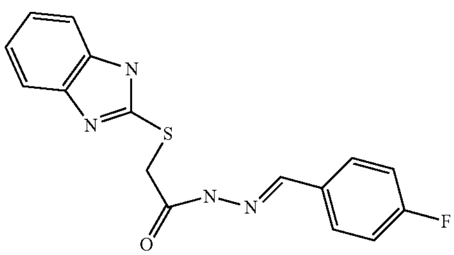 [SMILES: O=C(CSc1nc2ccccc2[nH]1)N/N=C/c1ccc(F)cc1] | KH7.129 |
| 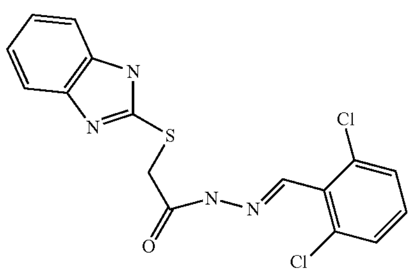 [SMILES: O=C(CSc1nc2ccccc2[nH]1)N/N=C/c1c(Cl)cccc1Cl] | KH7.130 |
| 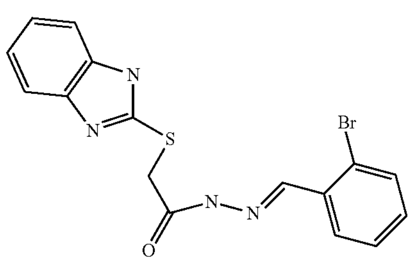 [SMILES: O=C(CSc1nc2ccccc2[nH]1)N/N=C/c1ccccc1Br] | KH7.131 |
| 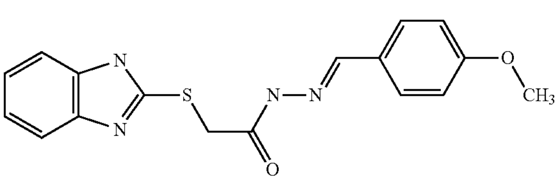 [SMILES: COc1ccc(/C=N/NC(=O)CSc2nc3ccccc3[nH]2)cc1] | KH7.132 |

TABLE 2-continued

| Structure | Name |
|---|---|
| 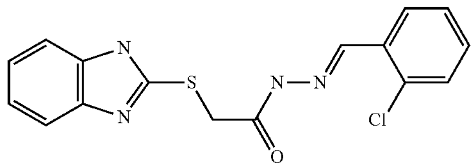 [SMILES: O=C(CSc1nc2ccccc2[nH]1)N/N=C/c1ccccc1Cl] | KH7.133 |
| 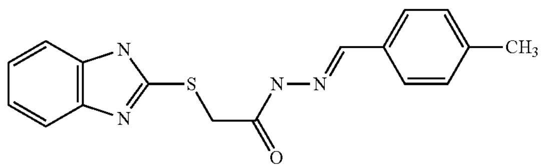 [SMILES: Cc1ccc(/C=N/NC(=O)CSc2nc3ccccc3[nH]2)cc1] | KH7.134 |
| 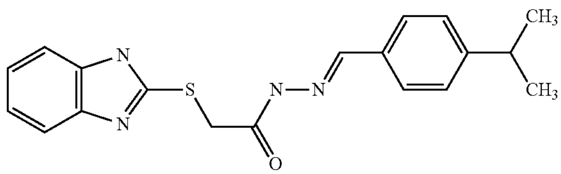 [SMILES: CC(C)c1ccc(/C=N/NC(=O)CSc2nc3ccccc3[nH]2)cc1] | KH7.135 |
| 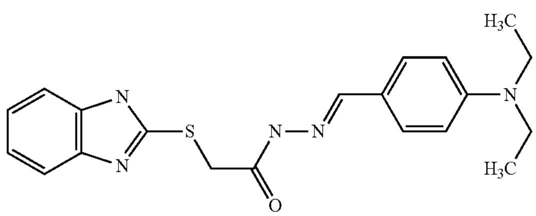 [SMILES: CCN(CC)c1ccc(/C=N/NC(=O)CSc2nc3ccccc3[nH]2)cc1] | KH7.136 |
| 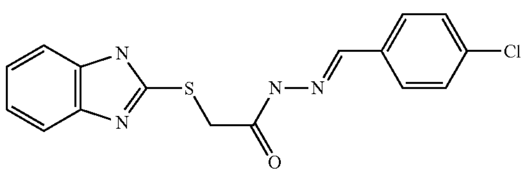 [SMILES: O=C(CSc1nc2ccccc2[nH]1)N/N=C/c1ccc(Cl)cc1] | KH7.137 |
| 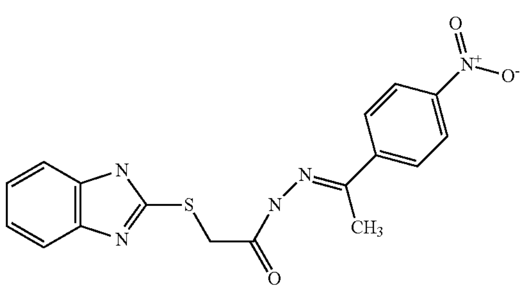 [SMILES: C/C(=N\NC(=O)CSc1nc2ccccc2[nH]1)c1ccc([N+](=O)[O-])cc1] | KH7.138 |
| 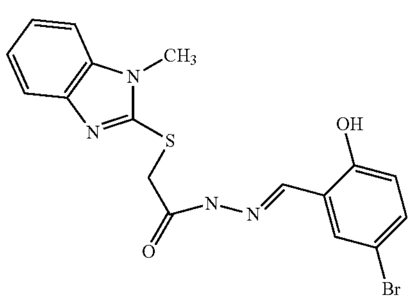 [SMILES: Cn1c(SCC(=O)N/N=C/c2cc(Br)ccc2O)nc2ccccc21] | KH7.139 |

TABLE 2-continued

| Structure | Name |
|---|---|
| 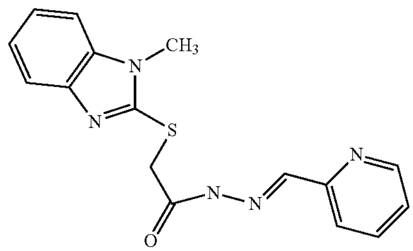 [SMILES: Cn1c(SCC(=O)N/N=C/c2ccccn2)nc2ccccc21] | KH7.140 |
| 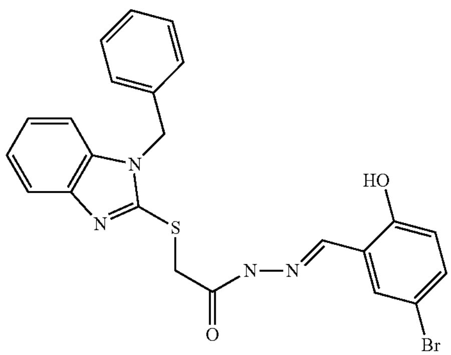 [SMILES: O=C(CSc1nc2ccccc2n1Cc1ccccc1)N/N=C/c1cc(Br)ccc1O] | KH7.141 |
| 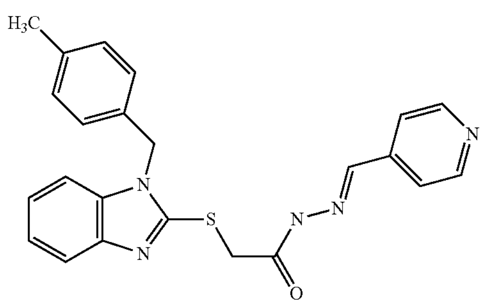 [SMILES: Cc1ccc(Cn2c(SCC(=O)N/N=C/c3ccncc3)nc3ccccc32)cc1] | KH7.142 |
| 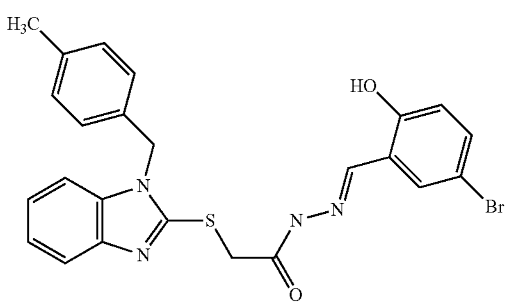 [SMILES: Cc1ccc(Cn2c(SCC(=O)N/N=C/c3cc(Br)ccc3O)nc3ccccc32)cc1] | KH7.143 |
| 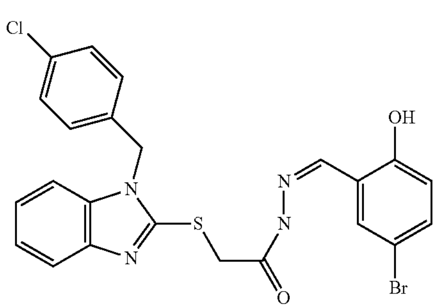 [SMILES: O=C(CSc1nc2ccccc2n1Cc1ccc(Cl)cc1)N/N=C\c1cc(Br)ccc1O] | KH7.144 |

TABLE 2-continued

| Structure | Name |
| --- | --- |
| 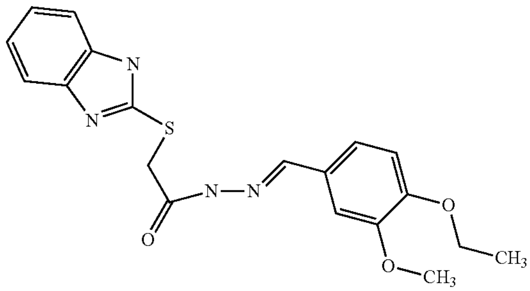 [SMILES: CCOc1ccc(/C=N/NC(=O)CSc2nc3ccccc3[nH]2)cc1OC] | KH7.145 |
| 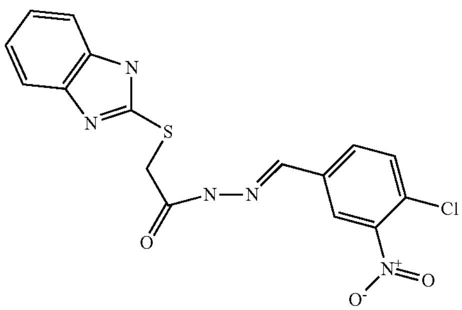 [SMILES: O=C(CSc1nc2ccccc2[nH]1)N/N=C/c1ccc(Cl)c([N+](=O)[O-])c1] | KH7.146 |
| 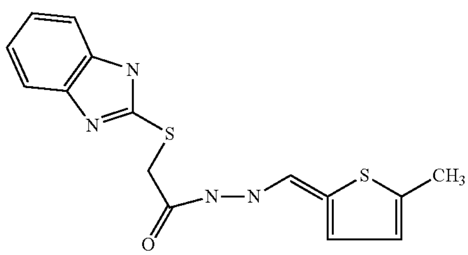 | KH7.147 |
| 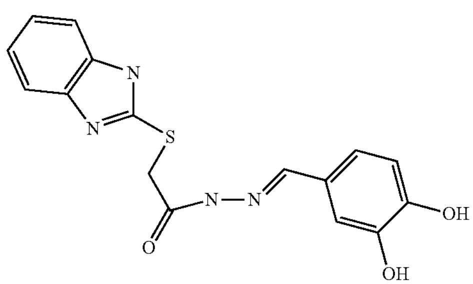 [SMILES: O=C(CSc1nc2ccccc2[nH]1)N/N=C/c1ccc(O)c(O)c1] | KH7.148 |
| 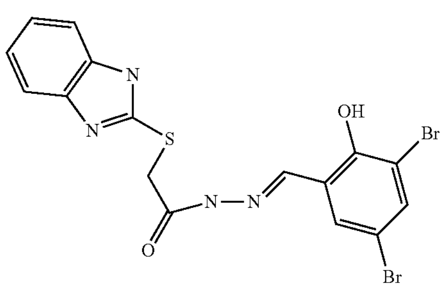 [SMILES: O=C(CSc1nc2ccccc2[nH]1)N/N=C/c1cc(Br)cc(Br)c1O] | KH7.149 |

TABLE 2-continued

| Structure | Name |
|---|---|
| 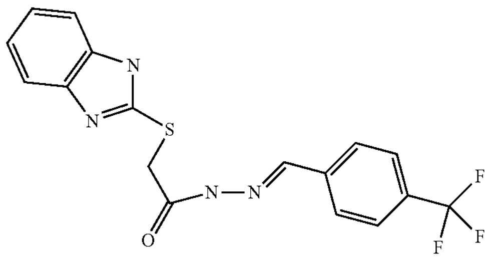 [SMILES: O=C(CSc1nc2ccccc2[nH]1)N/N=C/c1ccc(C(F)(F)F)cc1] | KH7.150 |
| 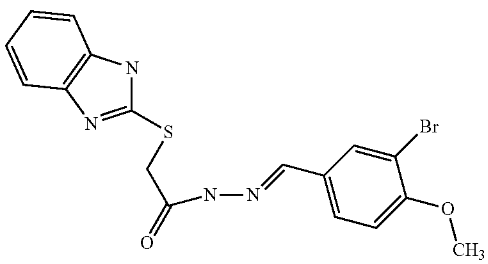 [SMILES: COc1ccc(/C=N/NC(=O)CSc2nc3ccccc3[nH]2)cc1Br] | KH7.151 |
| 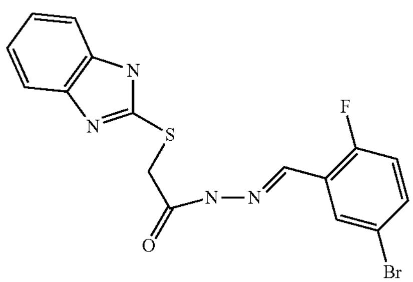 [SMILES: O=C(CSc1nc2ccccc2[nH]1)N/N=C/c1cc(Br)ccc1F] | KH7.152 |
| 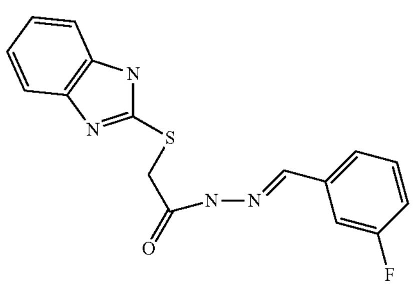 [SMILES: O=C(CSc1nc2ccccc2[nH]1)N/N=C/c1cccc(F)c1] | KH7.153 |
| 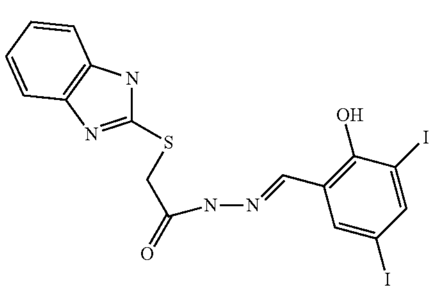 [SMILES: O=C(CSc1nc2ccccc2[nH]1)N/N=C/c1cc(I)cc(I)c1O] | KH7.154 |

TABLE 2-continued

| Structure | Name |
|---|---|
| [benzimidazole-S-CH2-C(O)-NH-N=CH-(2-Cl,5-NO2-phenyl)] | KH7.155 |
| [benzimidazole-S-CH2-C(O)-NH-N=CH-(5-Br-thiophene)] | KH7.156 |
| [benzimidazole-S-CH2-C(O)-NH-N=CH-(3-CH3-phenyl)] | KH7.157 |

Example 11

RNA Interference May be Used

One siRNA molecule against sAC corresponds to nucleotides 692-710 (CCAAGTGTATGGCCTTCAT) (SEQ ID No.3) relative to the first nucleotide of the start codon of rat sAC (GenBank accession No. AF081941). (See ref 25 and 26, incorporated herein in their entirety)

```
SEQUENCE 1: CTGGATATTCGAGTTAAGATA   (SEQ ID No. 1)
and sAC2
```

Another sAC siRNA molecule is directed against nucleotides 900-920 of rat sAC. (See ref 26)

```
SEQUENCE 2: TCGGAGCATGATTGAAATCGA   (SEQ ID No. 2)
```

Example 12

Figure 11:
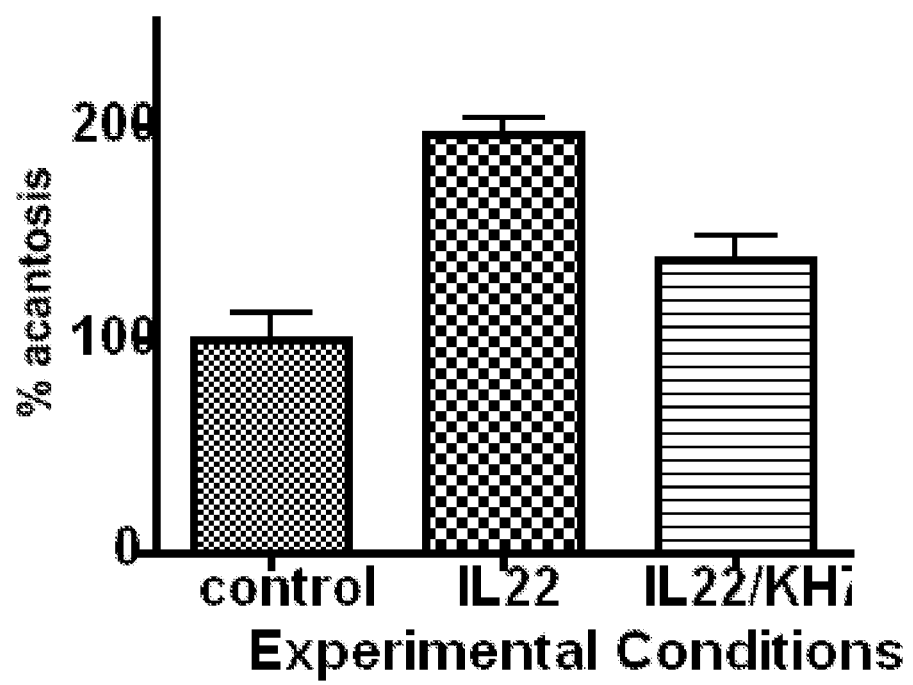
FIG. 11. Topical application of KH7 inhibits IL-22-induced acanthosis As before C57B1/6 mouse ears were injected with normal saline (control) or 500 ng of IL-22 in 20 microliters of normal saline (IL-22). After incubation for one hour the left ear was painted with 5 microliters of DMSO and the right ear was painted with 100 micromolar KH7 in DMSO (IL-22+KH7). This was repeated every other day for two weeks. The ears were then removed and the total area of acanthosis of each ear was calculated and represented as a % of acanthosis relative to control ears. These data are representative of three mice. ANOVA analysis found a statistically significant different P<0.05 between control and IL-22 treatments and between IL-22 and IL-22+KH7 treatments, but not between control and IL-22+KH7 treatments.

Topical application of KH7 inhibits IL-22-induced acanthosis. As before C57B1/6 mouse ears were injected with normal saline (control) or 500 ng of IL-22 in 20 microliters of normal saline (IL-22). After incubation for one hour the left ear was painted with 5 microliters of DMSO and the right ear was painted with 100 micromolar KH7 in DMSO (IL-22+KH7). This was repeated every other day for two weeks. The ears were then removed and the total area of acanthosis of each ear was calculated and represented as a % of acanthosis relative to control ears. The data is shown in FIG. 11; these data are representative of three mice. ANOVA analysis found a statistically significant different $P<0.05$ between control and IL-22 treatments and between IL-22 and IL-22+KH7 treatments, but not between control and IL-22+KH7 treatments.

---

The invention claimed is:

1. A method to inhibit hyperproliferative keratinocyte replication in a mammalian subject in need thereof, comprising:
administering to the subject a composition that inhibits soluble adenylyl cyclase in said mammalian keratinocyte, wherein the composition comprises a small molecule selected from the group consisting of Gossypol, 4-hydroxyestradiol, 2-hydroxyestradiol, 2-hydroxyestrone, 2-benzimidazolylthioacetamide-N-ethyl-2-benzyl (KH7.102), the compound of formula I (KH1)

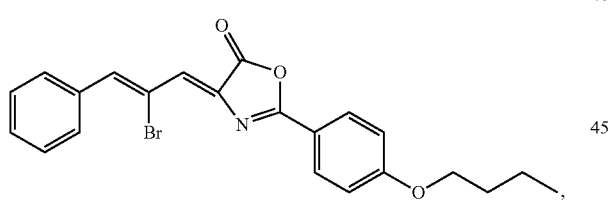

formula I the compound of formula II (KH2)

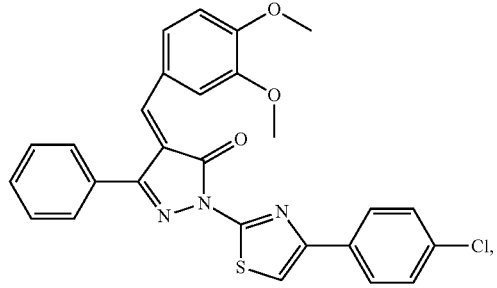

formula II the compound of formula III (KH3)

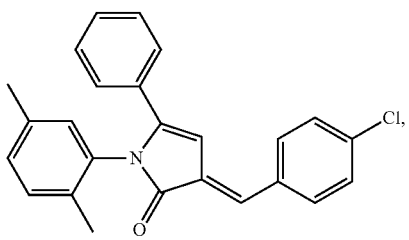

formula III the compound of formula IV (KH4)

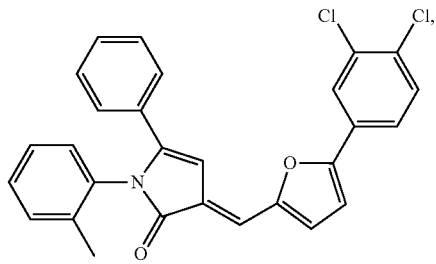

formula IV the compound of formula V (KH8)

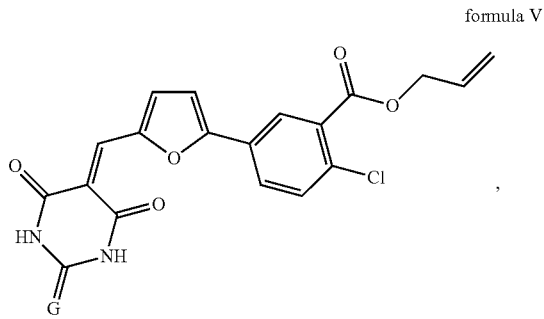

the compound of formula VI (KH7.120)

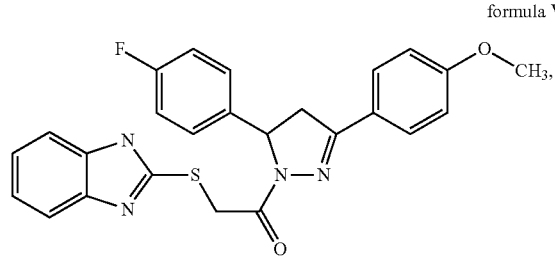

and a compound of formula VII

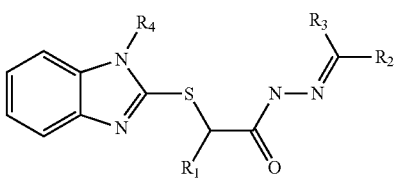

wherein $R_1$ and $R_3$ are each independently H or a $C_{1-4}$ alkyl $R_2$ is a $C_{6-8}$ aryl, naphthalene or a $C_{4-5}$ heteroaryl having at least one hetero atom selected from N, S and O, the phenyl or $C_{4-5}$ heteroaryl optionally substituted with one or more radicals selected from the group consisting of hydroxyl, halogen, nitro, $C_{1-4}$ alkyl, $C_{1-4}$ alkoxy, $C_{1-4}$ carboxyl, phenyl, $C_{1-4}$ alkoxy phenyl, and a halogenated $C_{1-4}$ alkyl, and $R_4$ is H, a $C_{1-4}$ alkyl, a $C_{1-4}$ carboxyl or a $C_{6-8}$ aryl, optionally substituted with a $C_{1-4}$ alkyl, a $C_{1-4}$ alkoxy, hydroxyl or a halogen.

2. The method according to claim 1, wherein the $C_{6-8}$ aryl is a phenyl or the $C_{4-6}$ heteroaryl is a pyridine, furan, or thiophene.

3. The method according to claim 1, wherein the small molecule is selected from the group of compounds consisting of Gossypol, 4-hydroxyestradiol, 2-hydroxyestradiol, 2-hydroxyestrone, 2-benzimidazolylthioacetamide-N-ethyl-2-benzyl (KH7.102),

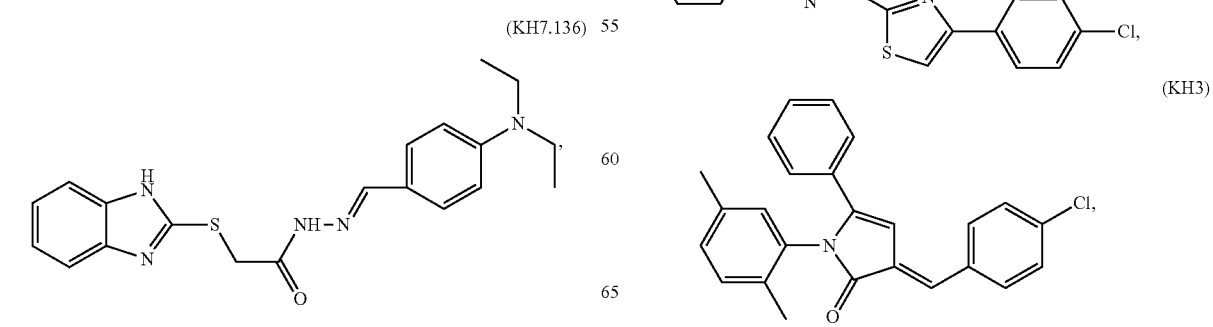

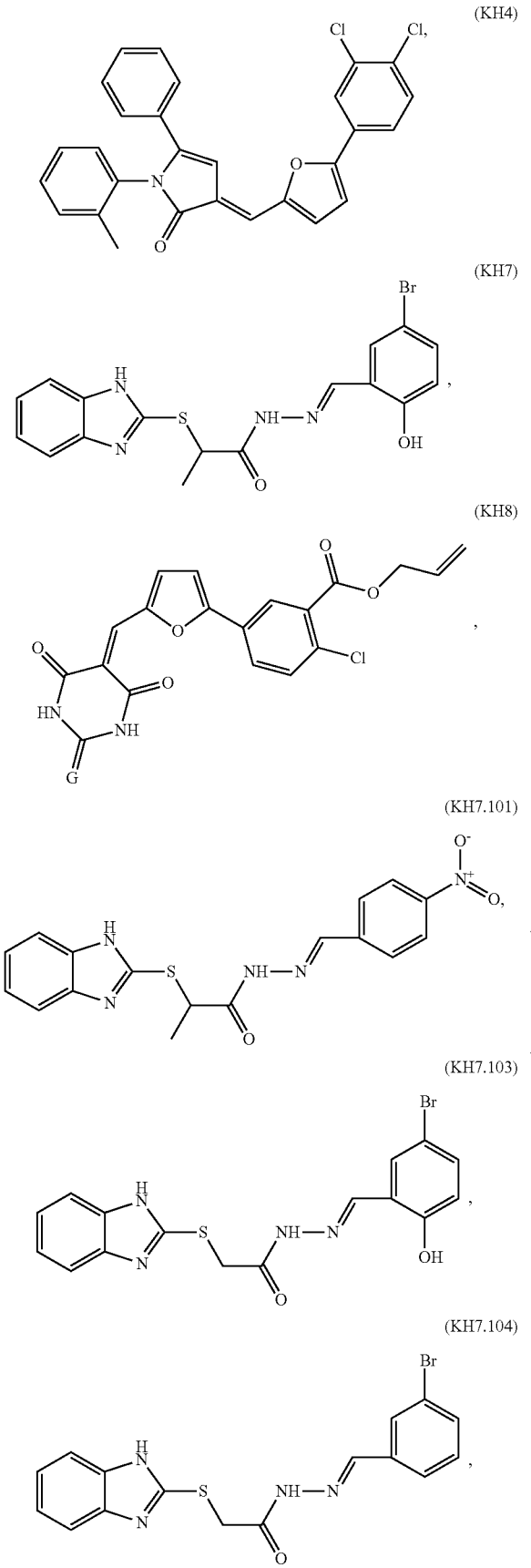
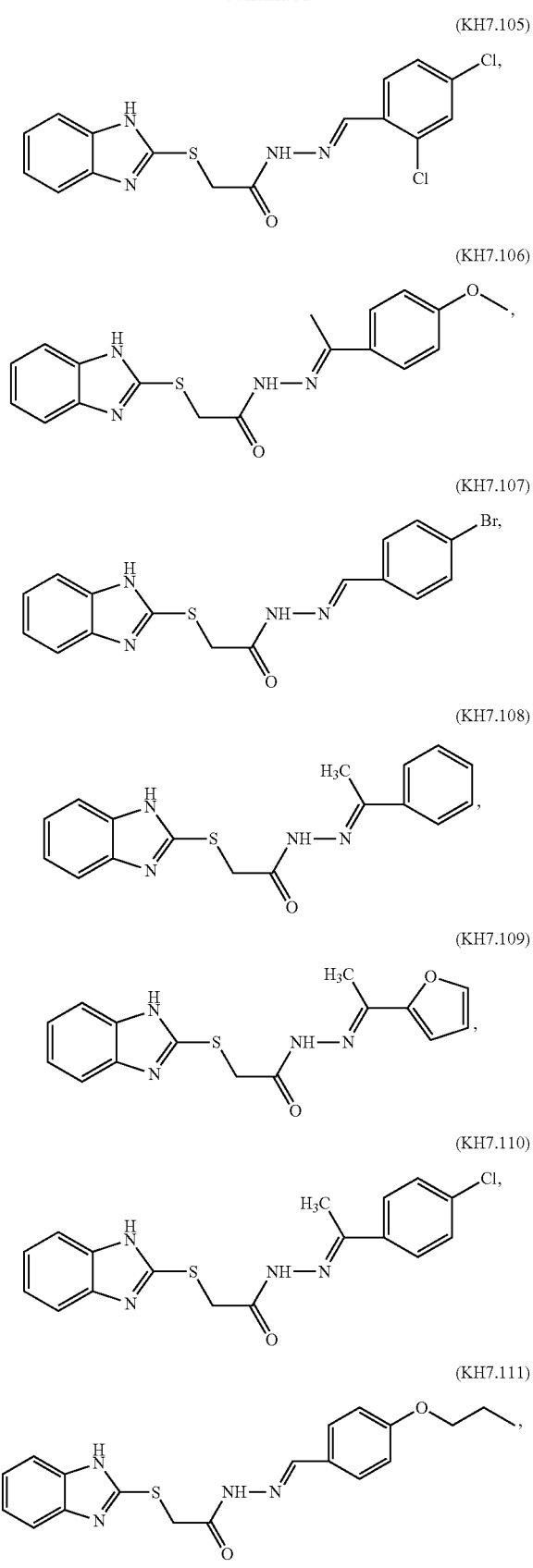

-continued
(KH7.112)
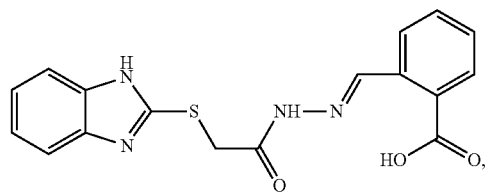
(KH7.113)
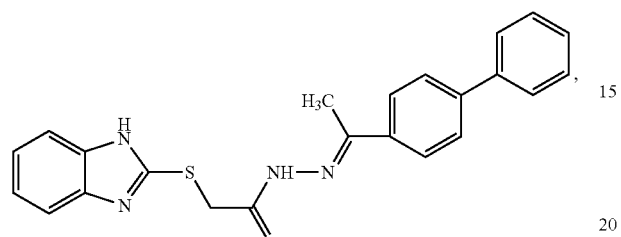
(KH7.114)
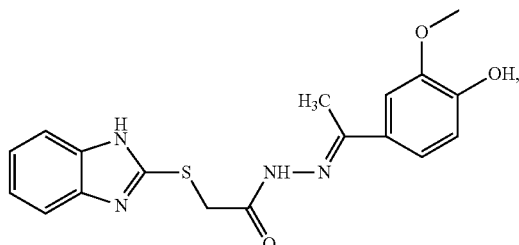
(KH7.115)
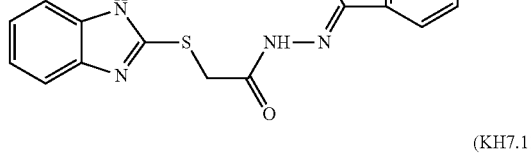
(KH7.116)
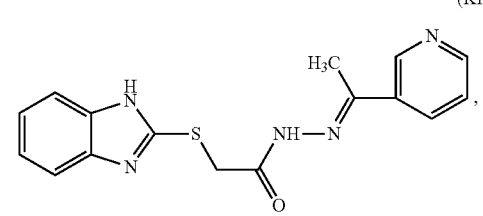
(KH7.117)
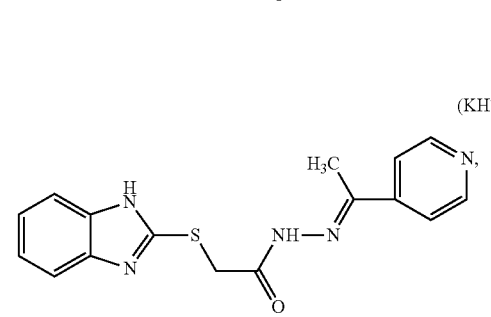
-continued
(KH7.118)
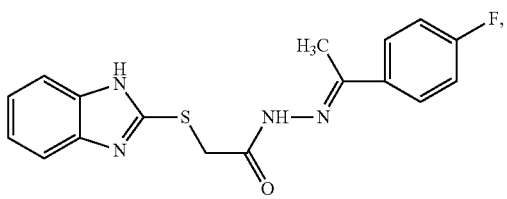
(KH7.119)
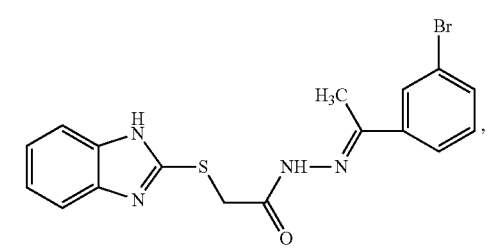
(KH7.120)
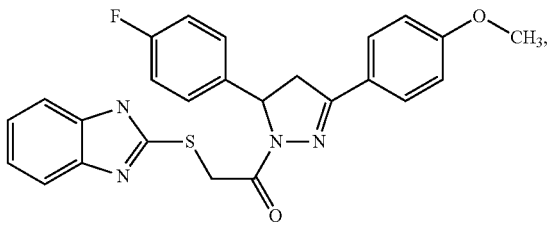
(KH7.121)
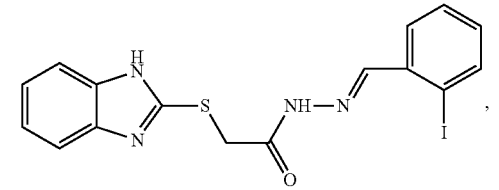
(KH7.122)
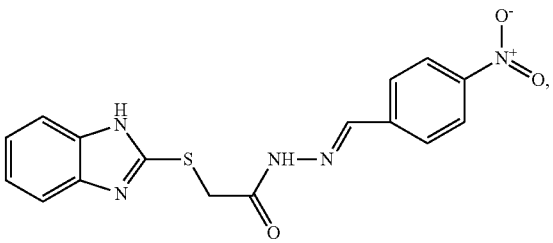
(KH7.123)
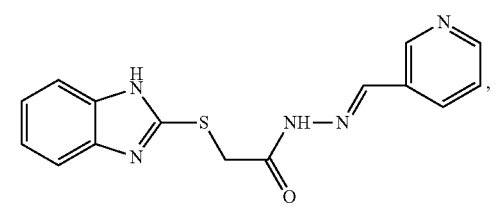

(KH7.124)
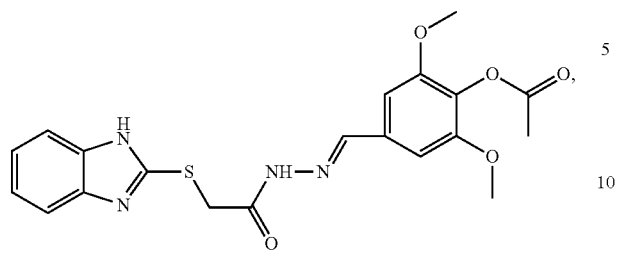
(KH7.125)
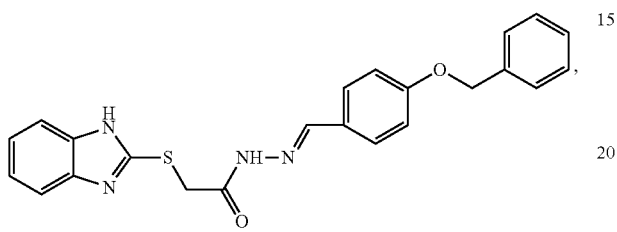
(KH7.126)
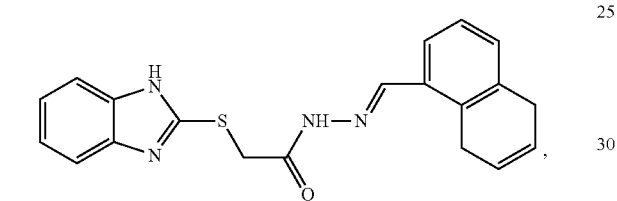
(KH7.127)
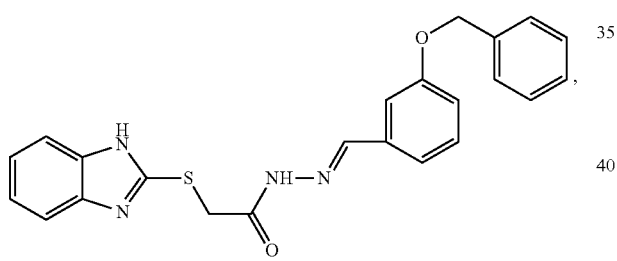
(KH7.128)
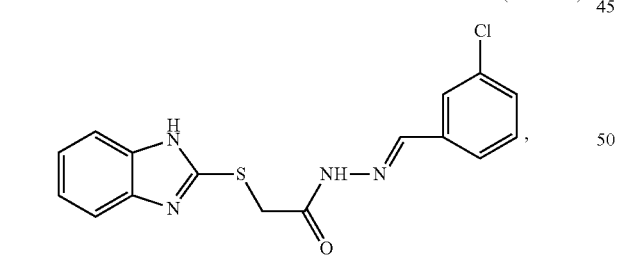
(KH7.129)
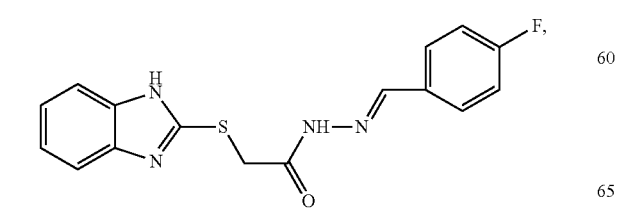
(KH7.130)
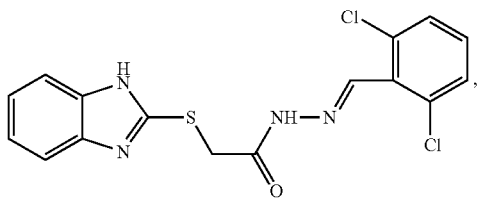
(KH7.131)
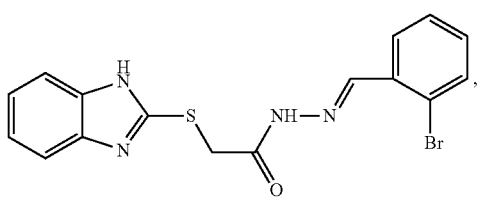
(KH7.132)
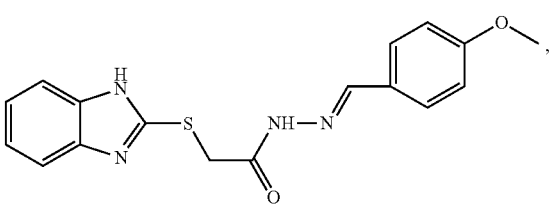
(KH7.133)
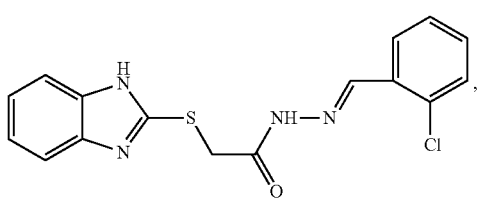
(KH7.134)
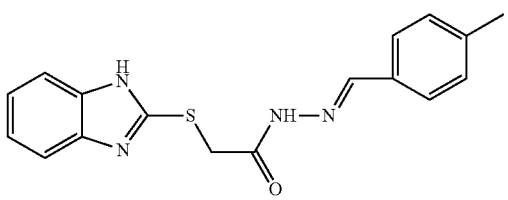
(KH7.135)
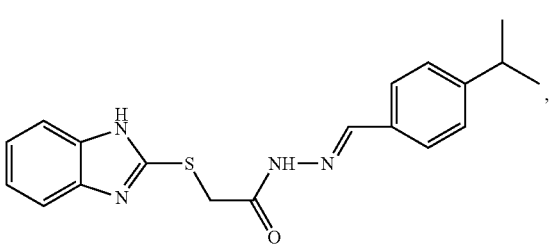

(KH7.136)
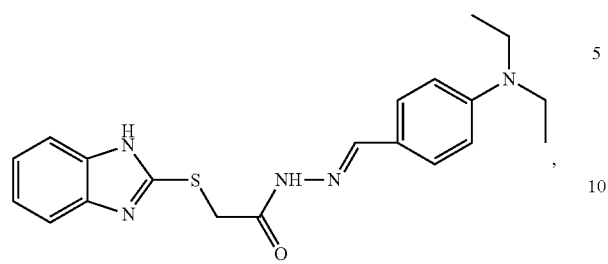
(KH7.137)
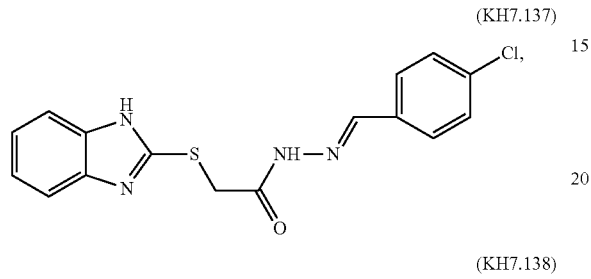
(KH7.138)
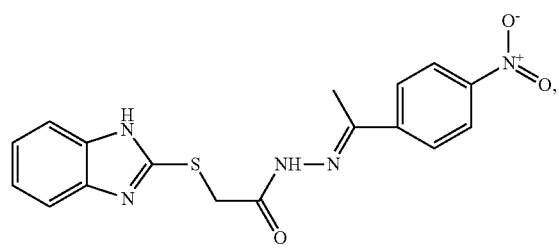
(KH7.139)
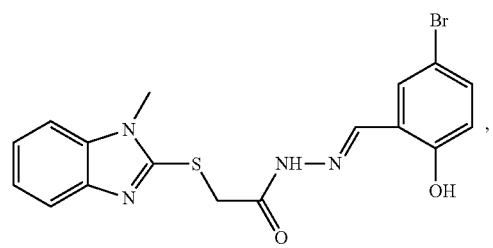
(KH7.140)
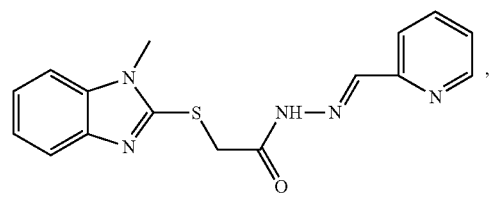
(KH7.141)
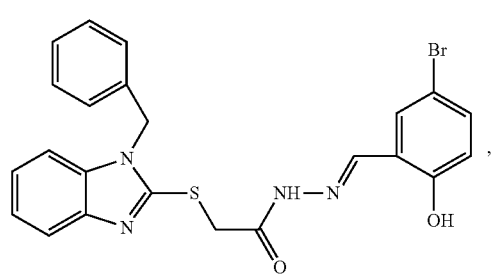
(KH7.142)
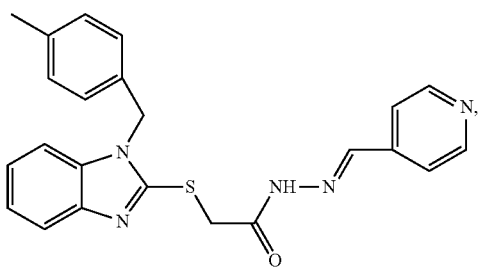
(KH7.143)
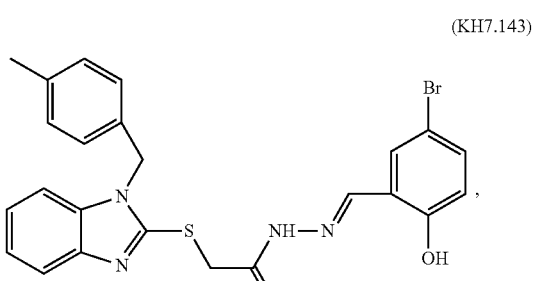
(KH7.144)
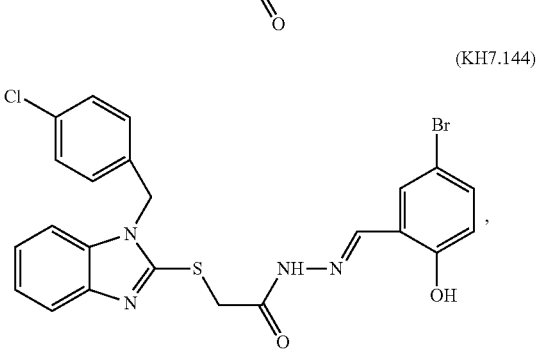
(KH7.145)
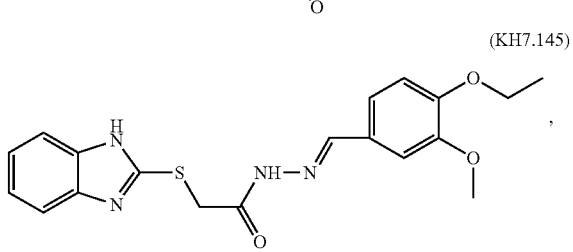
(KH7.146)
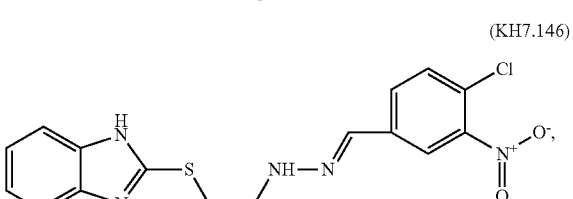
(KH7.147)
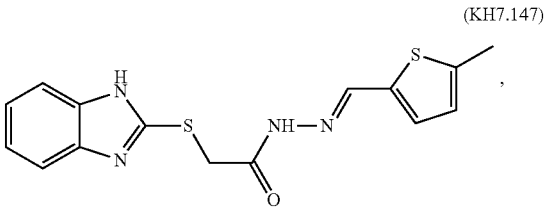

-continued
(KH7.148)
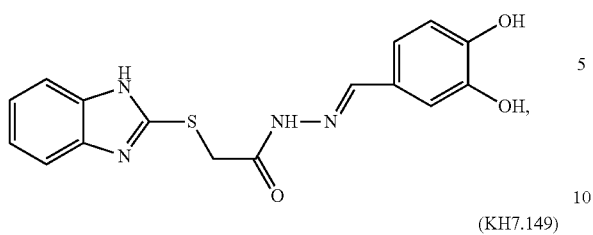
(KH7.149)
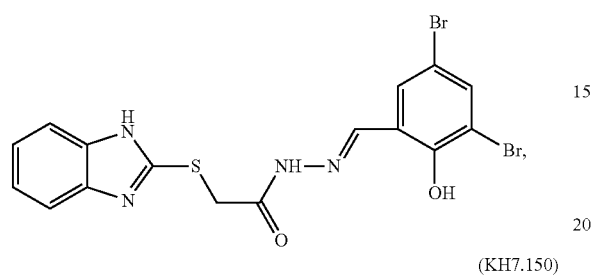
(KH7.150)
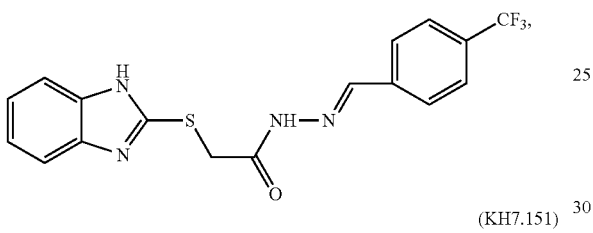
(KH7.151)
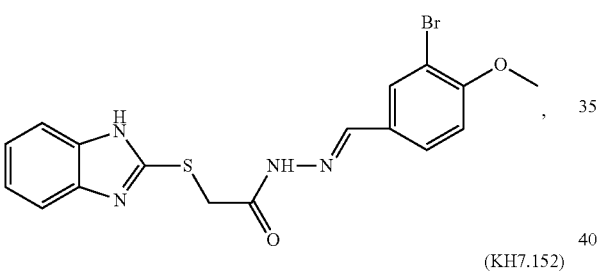
(KH7.152)
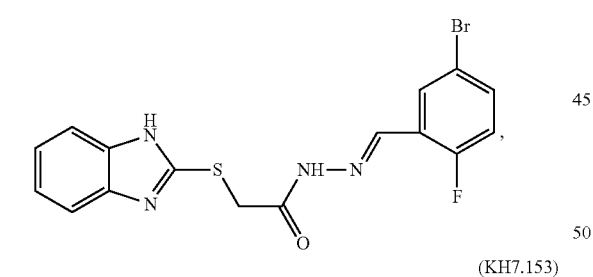
(KH7.153)
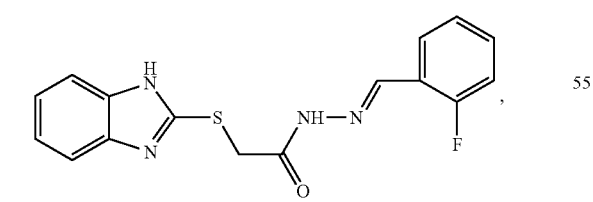
-continued
(KH7.154)
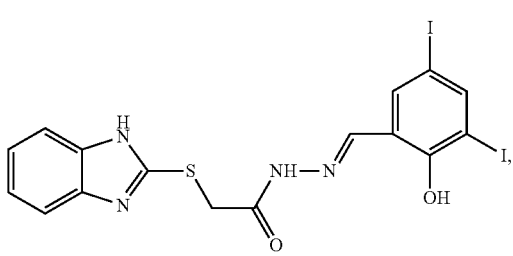
(KH7.155)
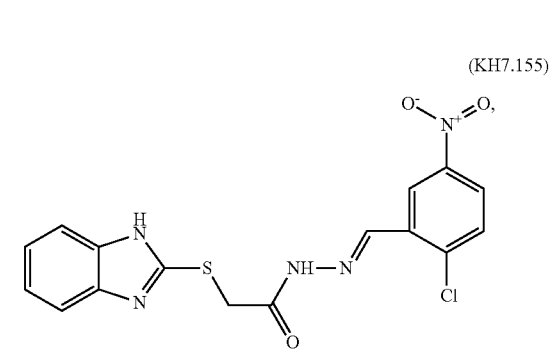
(KH7.156)
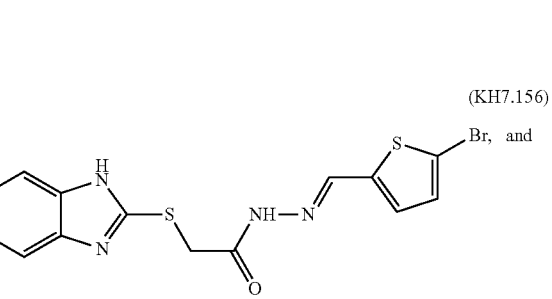
(KH7.157)
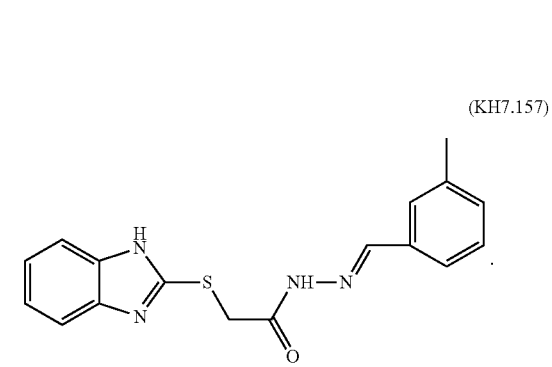
4. The method according to claim 1, wherein the mammal is a human.
5. The method according to claim 1, wherein the composition is administered topically, systemically, injected intradermally, or injected epidermally.
* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Unknown
<220> FEATURE:
```

```
<223> OTHER INFORMATION: synthetic

<400> SEQUENCE: 1
ctggatattc gagttaagat a                                         21

<210> SEQ ID NO 2
<211> LENGTH: 21
<212> TYPE: DNA
<213> ORGANISM: Unknown
<220> FEATURE:
<223> OTHER INFORMATION: synthetic

<400> SEQUENCE: 2
tcggagcatg attgaaatcg a                                         21

<210> SEQ ID NO 3
<211> LENGTH: 19
<212> TYPE: DNA
<213> ORGANISM: Rattus sp.

<400> SEQUENCE: 3
ccaagtgtat ggccttcat                                            19
```